(12) United States Patent
Millar et al.

(10) Patent No.: US 8,431,347 B2
(45) Date of Patent: Apr. 30, 2013

(54) ISOTHERMAL STRAND DISPLACEMENT AMPLIFICATION USING PRIMERS CONTAINING A NON-REGULAR BASE

(75) Inventors: Douglas Spencer Millar, Revesby (AU); John R. Melki, Dolls Point (AU); Geoffrey W. Grigg, Linley Point (AU); Ailsa Grigg, legal representative, Glebe (AU)

(73) Assignee: Human Genetic Signatures Pty Ltd (AU)

( * ) Notice: Subject to any disclaimer, the term of this patent is extended or adjusted under 35 U.S.C. 154(b) by 886 days.

(21) Appl. No.: 11/919,443

(22) PCT Filed: May 25, 2006

(86) PCT No.: PCT/AU2006/000698
§ 371 (c)(1),
(2), (4) Date: Nov. 17, 2009

(87) PCT Pub. No.: WO2006/125267
PCT Pub. Date: Nov. 30, 2006

(65) Prior Publication Data
US 2010/0221785 A1    Sep. 2, 2010

Related U.S. Application Data

(60) Provisional application No. 60/685,697, filed on May 26, 2005.

(51) Int. Cl.
*C12Q 1/68* (2006.01)
*C12P 19/34* (2006.01)

(52) U.S. Cl.
USPC ........................................ 435/6.12; 435/91.2

(58) Field of Classification Search .......................... None
See application file for complete search history.

(56) References Cited

U.S. PATENT DOCUMENTS

| | | |
|---|---|---|
| 5,175,273 A | 12/1992 | Bischofberger et al. |
| 5,414,077 A | 5/1995 | Lin et al. |
| 5,418,149 A | 5/1995 | Gelfand et al. |
| 5,629,156 A | 5/1997 | Shah et al. |
| 5,656,744 A | 8/1997 | Arnold et al. |
| 5,750,338 A | 5/1998 | Collins et al. |
| 5,786,146 A | 7/1998 | Herman et al. |
| 5,824,517 A | 10/1998 | Cleuziat et al. |
| 5,952,174 A | 9/1999 | Nikiforov et al. |
| 6,156,501 A | 12/2000 | McGall et al. |
| 6,251,637 B1 | 6/2001 | Blusch |
| 6,265,171 B1 | 7/2001 | Herman et al. |
| 6,331,393 B1 | 12/2001 | Laird et al. |
| 6,420,106 B1 | 7/2002 | Gyllensten et al. |
| 6,521,411 B2 | 2/2003 | Hecker et al. |
| 6,692,918 B2 | 2/2004 | Kurn |
| 6,960,436 B2 | 11/2005 | Cottrell |
| 7,008,770 B1 | 3/2006 | Berlin |
| 7,288,373 B2 | 10/2007 | Millar et al. |
| 7,413,855 B2 | 8/2008 | Bergmann et al. |
| 7,504,207 B2 | 3/2009 | Bergquist et al. |
| 7,527,948 B2 | 5/2009 | Hudson et al. |
| 7,799,525 B2 | 9/2010 | Millar |
| 7,803,580 B2 | 9/2010 | Millar |
| 7,833,942 B2 | 11/2010 | Millar et al. |
| 7,846,693 B2 | 12/2010 | Millar et al. |
| 8,168,777 B2 | 5/2012 | Millar et al. |
| 2002/0086324 A1 | 7/2002 | Laird et al. |
| 2002/0142397 A1 | 10/2002 | Collas et al. |
| 2003/0073081 A1 | 4/2003 | Mukai et al. |
| 2003/0082600 A1 | 5/2003 | Olek et al. |
| 2003/0119025 A1 | 6/2003 | Olek et al. |
| 2003/0143577 A1 | 7/2003 | Hogrefe et al. |
| 2004/0067559 A1 | 4/2004 | McCarthy et al. |
| 2004/0086944 A1 | 5/2004 | Grigg et al. |
| 2004/0203004 A1 | 10/2004 | Bernard et al. |
| 2004/0219539 A1 | 11/2004 | Millar et al. |

(Continued)

FOREIGN PATENT DOCUMENTS

| | | |
|---|---|---|
| DE | 103 31 107 B3 | 12/2004 |
| EP | 1 130 113 | 9/2001 |
| EP | 1 319 718 | 6/2003 |
| EP | 1 443 052 | 8/2004 |
| EP | 1 801 213 A2 | 6/2007 |
| WO | WO 95/01456 | 1/1995 |
| WO | WO 95/22623 | 8/1995 |
| WO | WO 97/41254 | 11/1997 |
| WO | WO 97/45559 | 12/1997 |
| WO | WO 98/20157 | 5/1998 |

(Continued)

OTHER PUBLICATIONS

International Search Report issued on the corresponding PCT Application No. PCT/AU2006/000698, dated Aug. 1, 2006.

International Preliminary Report on Patentability issued on the corresponding PCT Application No. PCT/AU2006/000698, dated Apr. 20, 2007.

Asseline et al. Synthesis and binding properties of oligonucleotides covalently linked to an acridine derivative: New study of the influence of the dye attachment site. Bioconjugate Chem., 7:369-379 (1996).

(Continued)

*Primary Examiner* — Kenneth R. Horlick
*Assistant Examiner* — David Thomas
(74) *Attorney, Agent, or Firm* — Knobbe Martens Olson & Bear, LLP

(57) ABSTRACT

The invention is directed to a method for isothermal DNA amplification comprising providing to the DNA to be amplified an amplification mix comprising a first primer at least partially complementary to a region of DNA and containing a non-regular base, a second primer at least partially complementary to a region of DNA and containing a non-regular base, a DNA polymerase, an enzyme capable of strand displacement, an enzyme that recognises a non-regular base in double-stranded DNA and causes a nick or excises a base in one DNA strand at or near the non-regular base; and amplifying the DNA substantially without thermal cycling.

58 Claims, 5 Drawing Sheets

U.S. PATENT DOCUMENTS

| | | | |
|---|---|---|---|
| 2005/0019762 A1 | 1/2005 | Olek | |
| 2005/0059003 A1 | 3/2005 | Enoki et al. | |
| 2005/0118578 A1 | 6/2005 | Mineno et al. | |
| 2005/0136417 A1* | 6/2005 | Cole et al. | 435/6 |
| 2005/0196392 A1 | 9/2005 | Andersen | |
| 2005/0196792 A1* | 9/2005 | Fodor et al. | 435/6 |
| 2005/0202490 A1 | 9/2005 | Makarov | |
| 2006/0014144 A1 | 1/2006 | Christensen et al. | |
| 2006/0051771 A1 | 3/2006 | Murphy et al. | |
| 2006/0068406 A1 | 3/2006 | Affholter et al. | |
| 2006/0094009 A1* | 5/2006 | Vaughan et al. | 435/6 |
| 2006/0166203 A1 | 7/2006 | Tooke | |
| 2006/0286576 A1 | 12/2006 | Lofton-Day | |
| 2007/0020633 A1 | 1/2007 | Millar et al. | |
| 2007/0020639 A1 | 1/2007 | Shapiro | |
| 2007/0020653 A1 | 1/2007 | Holliger et al. | |
| 2007/0026070 A1 | 2/2007 | Vonwiller et al. | |
| 2007/0042365 A1 | 2/2007 | Millar et al. | |
| 2007/0065824 A1 | 3/2007 | Gutig | |
| 2007/0178457 A1 | 8/2007 | Millar | |
| 2007/0178459 A1 | 8/2007 | Millar et al. | |
| 2007/0190530 A1 | 8/2007 | Birkner et al. | |
| 2007/0264653 A1 | 11/2007 | Berlin et al. | |
| 2008/0050738 A1 | 2/2008 | Millar | |
| 2009/0029346 A1 | 1/2009 | Millar et al. | |
| 2009/0042732 A1 | 2/2009 | Millar et al. | |
| 2009/0130657 A1 | 5/2009 | Millar | |
| 2009/0263909 A1 | 10/2009 | Millar et al. | |
| 2010/0041013 A1 | 2/2010 | Millar et al. | |
| 2010/0092972 A1 | 4/2010 | Millar et al. | |
| 2010/0121056 A1 | 5/2010 | Christensen et al. | |
| 2010/0286379 A1 | 11/2010 | Millar et al. | |
| 2010/0304386 A1 | 12/2010 | Millar | |
| 2011/0003700 A1 | 1/2011 | Millar | |
| 2011/0136098 A1 | 6/2011 | Millar et al. | |
| 2012/0021461 A1 | 1/2012 | Millar et al. | |

FOREIGN PATENT DOCUMENTS

| | | |
|---|---|---|
| WO | WO 98/29108 | 7/1998 |
| WO | WO 99/09211 A2 | 2/1999 |
| WO | WO 99/14226 | 3/1999 |
| WO | WO 99/49081 A2 | 9/1999 |
| WO | WO 00/44934 | 8/2000 |
| WO | WO 00/50869 A2 | 8/2000 |
| WO | WO 01/09374 A2 | 2/2001 |
| WO | WO 01/38565 A2 | 5/2001 |
| WO | WO 01/42493 A2 | 6/2001 |
| WO | WO 01/76451 A2 | 10/2001 |
| WO | WO 02/36821 A2 | 5/2002 |
| WO | WO 02/38801 | 5/2002 |
| WO | WO 02/46452 | 6/2002 |
| WO | WO 02/072880 | 9/2002 |
| WO | WO 02/097065 | 12/2002 |
| WO | WO 03/008623 A2 | 1/2003 |
| WO | WO 03/048732 | 6/2003 |
| WO | WO 03/051901 A2 | 6/2003 |
| WO | WO 03/052132 A2 | 6/2003 |
| WO | WO 03/052133 A2 | 6/2003 |
| WO | WO 03/052134 A2 | 6/2003 |
| WO | WO 2004/015139 | 2/2004 |
| WO | WO 2004/065625 | 8/2004 |
| WO | WO 2004/090166 | 10/2004 |
| WO | WO 2004/096825 | 11/2004 |
| WO | WO 2004/111266 | 12/2004 |
| WO | WO 2005/021778 | 3/2005 |
| WO | WO 2005/056790 A1 | 6/2005 |
| WO | WO 2005/113760 | 12/2005 |
| WO | WO 2006/058393 | 6/2006 |
| WO | WO 2006/066353 | 6/2006 |
| WO | WO 2006/113770 | 10/2006 |
| WO | WO 2006/125267 | 11/2006 |
| WO | WO 2007/106802 A2 | 9/2007 |
| WO | WO 2008/109945 | 9/2008 |
| WO | WO 2008/135512 | 11/2008 |
| WO | WO 2008/150998 | 12/2008 |
| WO | WO 2009/067743 | 6/2009 |
| WO | WO 2009/070843 | 6/2009 |
| WO | WO 2009/079703 | 7/2009 |

OTHER PUBLICATIONS

Badal V. et al: "CpG methylation of human papilomavirus type 16 DNA in cervical cancer cell lines and in clinical specimens: Genomic hypomethylation correlates with carcinogenic progression" J Virol., 77(11): 6227-6234(Jun. 1, 2003).

Badal et al. The human papillomavirus-18 genome is efficiently targeted by cellular DNA methylation, Virology 324(2): 483-492 (Jul. 1, 2004).

Bakker, et al., Methyl-CpG Binding Domain Protein 2 Represses Transcription from Hypermethylated gamma-Class Glutathione *S-Transferase Gene Promoters in Hepatocellular Carcinoma Cells*, JBC, 277(25): 22573-22580, Jun. 2002.

Baleriola et al. Comparison of a novel HPV test with the Hybrid Capture II (hcII) and a reference PCR method shows high specificity and positive predictive value for 13 high-risk human papillomavirus infections J Clin Vir., 42(1): 22-26 (May 1, 2008).

Bleczinski et al. Steroid-DNA interactions increasing stability, sequence-selectivity, DNA/RNA discrimination, and hypochromicity of oligonucleotide duplexes. J. Am. Chem. Soc. 121:10889-10894 (1999).

Burmeister et al. Synthesis of novel phosphoramidite derivatives bearing pyrenyl and dansyl groups. Tetrahedron Letters. 36(21):3667-3668 (1995).

Cameron et al. Neoplasia: CpG island methylation in primary acute leukemia is heterogeneous and suggests density as a critical factor for transcriptional silencing, Blood, 94(7): 2445-2451, Oct. 1999.

Christensen et al. Intercalating nucleic acids containing insertions of 1-*O*-(1-pyrenylmethyl) glycerol: stabilisation of dsDNA and discrimination of DNA over RNA. Nucleic Acids Research. 30(22):4918-4925 (2002).

Clark et al. Bisulphite genomic sequencing of methylated cytosines. Laboratory Methods for the Detection of Mutations and Polymorphisms in DNA. Graham R. Taylor, Ed. CRC Press, New York (1997), pp. 151-162.

Clark et al. High sensitivity mapping methylated cytosines. Nucleic Acids Research, 22(15): 2990-2997 (1994).

Cohen et al, Hypermethylation of CpG Island Loci of Multiple Tumor Suppressor Genes in Retinoblastoma, Experimental Eye Research, 86(2): 201-206 (2008).

Cottrell et al., A real-time PCR assay for DNA-methylation-specific blockers. Nucleic Acid Research, 32(1):e10 (8 pages). Jan. 13, 2004.

D'Abbadie, et al., "Molecular Breeding of Polymerases for Amplification of Ancient DNA," Nature Biotechnology, (Aug. 2007) 25:939-943.

De Mesmaeker et al. Amide backbone modifications for antisense oligonucleotides carrying potential intercalating substituents: Influence on the thermodynamic stability of the corresponding duplexes with RNA- and DNA-complements. Bioorganic & Medicinal Chemistry Letters. 7(14):1869-1874 (1997).

Dean et al. Comprehensive human genome amplification using multiple displacement amplification. PNAS, 99(8): 5261-5266 (2002).

Eads, et al. MethyLight: a high-throughput assay to measure DNA methylation. Nucleic Acids Research, 28(8): E32.1-E32.8. (2000).

Esteller, et al., Inactivation of Glutathione S-Transferase *P1* Gene by Promoter Hypermethylation in Human Neoplasia, Cancer Research, 58: 4514-4518, Oct. 1998.

Feil et al. Methylation analysis on individual chromosomes: improved protocol for bisulphite genomic sequencing. Nucleic Acids Research 22(4): 695-696 (1994).

Feng et al. Detection of hypermethylated genes in women with and without cervical neoplasia. J Nat Cancer Inst. 97(4): 273-282 (Feb. 16, 2005).

Francois et al. Recognition of hairpin-containing single-stranded DNA by oligonucleotides containing internal acridine derivatives. Bioconjugate Chem. 10:439-446 (1999).

Frommer, et al. "A genomic sequencing protocol that yields a positive display of 5-methylcytosine residues in individual DNA strands," Proc. Natl. Acad. Sci. 89: 1827-1831 (1992).

Grigoriev, et al. A Triple Helix-forming Oligonucleotide-Intercalator Conjugate Acts as a Transcriptional Repressor via Inhibition of NFkB Binding to Interleukin-2 Receptor a-Regulatory Sequence. J Biol Chem., 267 (5): 3389-3395 (1992).

Grunau, et al. " Bisulfite genomic sequencing: systematic investigation of critical experimental parameters." Nucleic Acids Research, (2001) vol. 29, No. 13e65, pp. 1-7.

Gu et al. Depletion of *Saccharomyces cerevisiae* tRNAHis Guanylyltransferase Thglp leads to uncharged tRNAH is with additional m5C, Mol Cell Biol. 25(18): 8191-8201 (Sep. 2005).

Håkelien et al. Reprogramming fibroblasts to express T-cell functions using cell extracts. Nature Biotechnology, 20(5): 460-466 (2002).

Håkelien et al. Novel Approaches to Transdifferentation. Cloning and Stem Cells. 4: 379-387 (2002).

Herman et al. Unit 10.6 Methylation-Specific PCR, Current Protocols in Human Genetics, Published Online: May 1, 2001, pp. 10.6.1-10.6.10, DOI: 10.1002/0471142905.hg1006s16, Copyright © 2003 by John Wiley and Sons, Inc: http://onlinelibrary.wiley.com/doi/10.1002/0471142905.hg1006s16/full.

Herman, et al. "Methylation-specific PCR: a novel PCR assay for methylation status of CpG islands." (1996) Proc. Natl. Acad. Sci. 93:9821-9826.

Hitchcock, T.M. et al, "Cleavage of deoxyoxadenosine-containing oligodeoxyribonucleotides by bacterial endonuclease V", Nucleic Acids Research, 2004, vol. 32, No. 13, pp. 4071-4080.

Hosono, et al. "Unbiased Whole-Genome Amplification Directly from Clinical Samples." Genome Research; 13:954-964 (2003).

International Human Genome Sequencing Consortium, "Initial sequencing and analysis of the human genome," Nature, 409(6822): 860-921 (2001).

Kalantari, et al. "Conserved methylation patterns of human papillomavirus type 16 DNA in asymptomatic infection and cervical neoplasia," Journal of Virology, vol. 78, No. 23, Dec. 2004, pp. 12762-12772.

Kim, et al. "DNA hypermethylation in gastric cancer" Alimentary Pharmacology & Therapeutics, vol. 20, No. Suppl. 1, Jul. 2004, pp. 131-142.

Kinoshita, et al. "Methylation of the androgen receptor minimal promoter silences transcription in human prostate cancer." Cancer Research, 60(13): 3623-3630 (Jul. 1, 2000).

Kono. Nuclear transfer and reprogramming. Reviews of Reproduction, 2(2): 74-80 (May 1997).

Korshun et al. Reagent for introducing pyrene residues in oligonucleotides. Bioconjugate Chern., 3: 559-562 (1992).

Kozak, et al.: "Influence of secondary structure on binding and migration of 40S ribosomal subunits," Cell, vol. 19, 1980, pp. 79-90.

Lee, et al. Cancer Epidemiology, Biomarkers, Prevention, vol. 6, pp. 443-450, Jun. 1997.

Longo, M.C. et al., Use of Uracil DNA Glycosylase to Control Carry-Over Contamination in Polymerase Chain Reactions, Gene, vol. 93, No. I, pp. 125-128, Sep. 1990.

Malyukova, et al. Methylation of the Putative Tumor Suppressor Gene RASSF1A in Primary Cervical Tumors, Mol Biol. 38( 6): 857-86, Nov. 2004.

Mann et al. Synthesis and properties of an oligodeoxynucleotide modified with a pyrene derivative at the 5'-phosphate. Bioconjugate Chern., 3: 554-558 (1992).

Masuko et al. Fluorescence resonance energy transfer from pyrene to perylene labels for nucleic acid hybridization assays under homogeneous solution conditions. Nucleic Acids Research, 28(8):e34, 8 pages (2000).

Melki, et al. Concurrent DNA Hypermethylation of Multiple Genes in Acute Myeloid Leukemia, Cancer Research, 59: 3730-3740, Aug. 1999.

Millar, et al. Detailed methylation analysis of the glutathione S-transferase pi (GSTPI) gene in prostate cancer, Oncogene 18(6): 1313-1324 (1999).

Millar, et al. A distinct sequence (ATAAA)n separates methylated and unmethylated domains at the 5'-end of the GSTPI CpG island. J. Biol. Chem., 275(32): 24893-24899 (2000).

Monk. Epigentic programming of differential gene expression in development and evolution. Dev. Genetics, 17: 188-197 (1995).

Munson, et al. Recovery of bisulphite-converted genomic sequences in the methylation-sensitive QPCR. Nucleic Acids Research (2007) 35(9): 2893-2903.

Narayan, et al. Frequent Promoter Methylation of CDH1, DAPK, RARB, and HIC1 Genes in Carcinoma of Cervix Uteri: Its Relationship to Clinical Outcome, Mol Cancer, 2(1): 24; May 2003, 12 pages. NCBI Database Accession No. M24485, Dec. 5, 1994.

Newton, et al. "The production of PCR products with 5' single-stranded tails using primers that incorporate novel phosphoramidite intermediates." Nucleic Acid Res. 21(5): 1155-1162 (1993).

Nilsson, et al. Padlock Probes: Circularizing Oligonucleotides for localized DNA Detection. Science; 265: 2085-2088 (1994).

Nousbaum, et al. Prospective Characteristics of Full-Length Hepatitis C Virus NS5A Quasispecies during. Induction and Combination Antiviral Therapy, J Virol., 74(19): 9028-9038 (2000).

Okada, et al. Sequence Determination of Rat U5 RNA Using a Chemical Modification Procedure for Counteracting Sequence Compression, (1982) J. Biochem. 91: 1281-1291.

Olek, et al. A modified and improved method for bisulphate based cytosine methylation analysis. (1996) Nucleic Acids Research, 24(24): 5064-5066.

Pao, et al. The endothelin receptor B (*EDNRB*) promoter displays heterogeneous, site specific methylation patterns in normal and tumor cells, Human Molecular Genetics, 10(9): 903-910, 2001.

Paris, et al. Probing DNA sequencs in solution with a monomer-excimer fluorescence color change. Nucleic Acids Research, 26(16):3789-3793 (1998).

Paulin, et al. Urea improves efficiency of bisulphite-mediated sequencing of 5'-methylcytosine in genomic DNA, Nucleic Acid Research, 26(21): 5009-5010 (Nov. 1, 1998).

Pietrobono, et al. Quantitative analysis of DNA demethylation and transcriptional reactivation of the FMR1 gene in fragile X cellstreated with 5-azadeoxycytidine. Nucleic Acids Research, 30(14): 3278-3285 (2002).

Raizis, et al. A Bisulfite method of 5-methylcytosine mapping that minimizes template degradation, Anal. Biochem., 226: 161-166 (1995).

Ratushna, et al. Secondary structure in the target as a confounding factor in synthetic oligomer microarray design, Genomics, 6(1): 31, Mar. 2005, 13 pages.

Rein, et al. Identifying 5-methylcytosine and related modifications in DNA genomes. Nucleic Acids Research, 26 (10): 2255-2264 (May 15,1998).

Robertson, et al. DNA methylation: past, present, and future directions. Carcinogenesis. 21(3): 461-467 (2000).

Robertson, et al. Methylation of the Epstein-Barr Virus Genome in normal Lymphocytes, Blood, 90: 4480-4484 (1997).

Sakaguchi, et al. Cautionary Note on the Use of dUMP-Containing PCR Primers with Pfu and VentR® DNA Polymerases. Biotechniques; 21(3): 368 & 370 (1996).

Sakashita, et al. Dynamic DNA methylation change in the CpG island region of p15 during human myeloid development, J. Clin. Invest., 108: 1195-1204 (2001).

Shao-Qing. Chinese journal of Agricultureal Biotechnology, vol. 4, No. 1, pp. 75-79, 2007.

Shapiro, et al. Deamination of cytosine derivatives by bisulfite. Mechanism of the reaction, J. Am. Chem. Soc., 96: 906-912 (1974).

Shibutani, et al., Translesional Synthesis on DNA Templates Containing a Single Abasic Site, J Biol Chem., 272(21): 13916-13922, 1997.

Shiraishi, et al. High Speed Conversion of Cytosine to Uracil in Bisulphite Genomic Sequencing Analysis of DNA Methylation; DNA Research,. 2: 409-415 (2004).

Stratagene, Gene Characterization Kit, 1988 Catalog, p. 39.

Tada, et al. Embryonic germ cells induce epigenetic reprogramming of somatic nucleus in hybrid cells. EMBO Journal, 16(21): 6510-6520 (1997).

Telenius, et al. Degenerate Oligonucleotide-Primed PCR: General Amplification of Target DNA by a Single Degenerate Primer, Genomics; 13(3): 718-725 (1992).

Timofeev et al. Methidium intercalator inserted into synthetic oligonucleotides. Tetrahedron Letters. 37(47):8467-8470 (1996).

Tohgi, et al. Decrease with age in methylcytosines in the promoter region of receptor for advanced glycated end products (RAGE) gene in autopsy human cortex, Molec Brain Res, 65: 124-128 (1999).

Toulmé et al. Specific inhibition of Mrna translation by complementary oligonucleotides covalently linked to intercalating agents. Proc Natl Acad Sci USA. 83:1227-1231 (1986).

Toyota, et al. Inactivation of *CACNA1G*, a T-Type Calcium Channel Gene, by Aberrant Methylation of Its 5' CpG Island in Human Tumors, Cancer Research, 59: 4535-4541, Sep. 1999.

Triplett, et al., Carbon-13 NMR Investigation of the bisulphite induced changes in yeast RNA; Biochemical and Biophysical Research Communications (1977), 77(4): 1170-1175.

Tsuda, et al. Relationship between HPV typing and abnormality of G1 cell cycle regulators in cervical neoplasm, Gynecologic Oncology, 91: 476-485, 2003.

Ushijima, et al. Aberrant methylations in cancer cells: Where do they come from? Cancer Science. 96(4): 206-211, Apr. 2005.

Venter, et al. The sequence of the human genome, Science, 291 (5523): 1304-1351 (2001).

Verma, Viral genes and methylation, Annals of the N.Y. Academy of Scuebces, 983: 170-180, Mar. 2003.

Virmani, et al. Aberrant Methylation during Cervical Carcinogenesis, Clin Cancer Res. 7(3): 584-489, Mar. 2001.

Wang et al. Comparison of bisulfite modification of 5-methyldeoxycytidine and deoxycytidine residues, Nucleic Acids Research, 8(2): 4777-4790 (1980).

Warnecke, et al. "Detection and measurement of PCR bias in quantitative methylation analysis of bisulphite-treated DNA," Nucleic Acids Research, vol. 25 No. 21, pp. 4422-4426, (1997).

Widschwendter et al: Analysis of aberrant DNA methylation and human papillomavirus DNA in cervicovaginal specimens to detect invasive cervical cancer and its precursors, Clin Cancer Res. 10(10): 3396-3400, May 2004.

Xiong, et al. Cobra: a sensitivite and quantitative DNA methylation assay. (1997) Nucleic Acids Research, 25 (12): 2532-2534.

Yamana et al. Synthesis and properties of oligonucleotides bearing a pendant pyrene group. Nucleic Acids Research. 16:169-172 (1985).

Yamana et al. Oligonucleotides having covalently linked anthracene at specific sugar residue: Differential binding to DNA and RNA and fluorescence properties. Tetrahedron Letters. 36(46):8427-8430 (1995).

Yamana et al. Incorporation of two anthraquinonylmethyl groups into the 2'-O-positions of oligonucleotides: Increased affinity and sequence specificity of anthraquinone-modified oligonucleotides in hybrid formation with DNA and RNA. Bioconjugate Chem., 7:715-720 (1996).

Yamana et al. Synthesis of oligonucleotide derivatives containing pyrene labeled glycerol linkers: enhanced excimer fluorescence on binding to a complementary DNA sequence. Tetrahedron Letters. 38(34): 6051-6054 (1997).

Yamana et al. 2'-Pyrene modified oligonucleotide provides a highly sensitive fluorescent probe of RNA. Nucleic Acids Research. 27(11):2387-2392 (1999).

Yanagi, et al. "Hepatitis C Virus: An infectious molecular clone of a second major genotype (2a) and lack of viability of intertypic 1a and 2a chimeras," Virology 262(1): 250-263 (1999).

Yao, M. et al, "Further Characterization of *Escherichia coli* Endonuclease V", Journal of Biological Chemistry, 1997, vol. 272, No. 49, pp. 30774-30779.

Zeschnigk, et al. "A novel real-time PCR assay for quantitative analysis of methylated alleles (QAMA): analysis of the retinoblastoma locus," Nucleic Acid Res. 2004, 32(16): 1-5.

Office Action in U.S. Appl. No. 10/561,029 dated Apr. 13, 2009.
Office Action in U.S. Appl. No. 10/561,029 dated Dec. 8, 2009.
Notice of Allowance issued in U.S. Appl. No. 10/561,029 dated May 28, 2010.
Office Action in U.S. Appl. No. 10/555,465 dated Oct. 1, 2008.
Notice of Abandonment in U.S. Appl. No. 10/555,465 dated Jun. 2, 2009.
Office Action in U.S. Appl. No. 10/428,310 dated Jan. 4, 2006.
Office Action in U.S. Appl. No. 10/428,310 dated Jul. 5, 2006.
Office Action in U.S. Appl. No. 10/428,310 dated Aug. 31, 2006.
Office Action in U.S. Appl. No. 10/428,310 dated Nov. 3, 2006.
Notice of Allowance in U.S. Appl. No. 10/428,310 dated May 24, 2007.
Notice of Allowance in U.S. Appl. No. 10/428,310 dated Sep. 21, 2007.
Office Action in U.S. Appl. No. 12/413,380 dated Mar. 11, 2011.
Office Action in U.S. Appl. No. 12/413,380 dated Nov. 3, 2011.
Notice of Allowance in U.S. Appl. No. 12/413,380 dated Jan. 9, 2012.
Office Action in U.S. Appl. No. 10/416,637 dated May 4, 2006.
Notice of Abandonment in U.S. Appl. No. 10/416,637 dated Jun. 15, 2007.
Office Action in U.S. Appl. No. 10/499,479 dated Dec. 20, 2006.
Office Action in U.S. Appl. No. 10/499,479 dated Apr. 19, 2007.
Office Action in U.S. Appl. No. 10/499,479 dated Jan. 3, 2008.
Office Action in U.S. Appl. No. 10/499,479 dated May 2, 2008.
Office Action in U.S. Appl. No. 10/499,479 dated May 30, 2008.
Office Action in U.S. Appl. No. 10/499,479 dated Feb. 5, 2009.
Notice of Abandonment in U.S. Appl. No. 10/499,479 dated Nov. 6, 2009.
Office Action in U.S. Appl. No. 12/534,743 dated May 14, 2010.
Notice of Abandonment in U.S. Appl. No. 12/534,743 dated Jan. 5, 2011.
Office Action in U.S. Appl. No. 11/660,586 dated Sep. 15, 2009.
Office Action in U.S. Appl. No. 11/660,586 dated Apr. 15, 2010.
Office Action in U.S. Appl. No. 11/660,586 dated Aug. 6, 2010.
Office Action in U.S. Appl. No. 11/660,586 dated Jul. 20, 2011.
Notice of Abandonment in U.S. Appl. No. 11/660,586 dated Mar. 7, 2012.
Office Action in U.S. Appl. No. 10/536,633 dated Apr. 4, 2007.
Office Action in U.S. Appl. No. 10/536,633 dated Jan. 25, 2007.
Notice of Abandonment in U.S. Appl. No. 10/536,633 dated Jan. 18, 2008.
Office Action in U.S. Appl. No. 11/919,443 dated Feb. 2, 2012.
Office Action in U.S. Appl. No. 11/919,443 dated May 29, 2012.
Office Action in U.S. Appl. No. 10/543,017 dated Aug. 8, 2007.
Office Action in U.S. Appl. No. 10/543,017 dated Oct. 19, 2007.
Office Action in U.S. Appl. No. 10/543,017 dated Jun. 20, 2008.
Office Action in U.S. Appl. No. 10/543,017 dated Dec. 8, 2008.
Notice of Abandonment in U.S. Appl. No. 10/543,017 dated Jun. 26, 2009.
Office Action in U.S. Appl. No. 10/570,715 dated Dec. 14, 2009.
Office Action in U.S. Appl. No. 10/570,715 dated Apr. 15, 2010.
Notice of Allowance in U.S. Appl. No. 10/570,715 dated Jul. 30, 2010.
Office Action in U.S. Appl. No. 11/573,873 dated May 4, 2009.
Office Action in U.S. Appl. No. 11/573,873 dated Sep. 2, 2009.
Office Action in U.S. Appl. No. 11/573,873 dated Mar. 23, 2010.
Notice of Allowance issued in U.S. Appl. No. 11/573,873, mailed Jul. 1, 2010.
Notice of Allowance issued in U.S. Appl. No. 11/575,060, mailed Jun. 15, 2010.
Office Action in U.S. Appl. No. 11/756,534 dated Aug. 10, 2009.
Office Action in U.S. Appl. No. 11/756,534 dated Feb. 22, 2010.
Office Action in U.S. Appl. No. 11/756,534 dated Jun. 8, 2010.
Office Action in U.S. Appl. No. 11/756,534 dated Oct. 20, 2010.
Notice of Abandonment in U.S. Appl. No. 11/756,534 dated May 12, 2011.
Office Action in U.S. Appl. No. 12/531,482 dated Jan. 17, 2012.
Office Action in U.S. Appl. No. 12/066,644 dated Apr. 22, 2010.
Office Action in U.S. Appl. No. 12/066,644 dated Sep. 23, 2010.
Office Action in U.S. Appl. No. 12/066,644 dated Mar. 13, 2012.
Notice of Abandonment in U.S. Appl. No. 12/227,962 dated Sep. 28, 2011.
Office Action in U.S. Appl. No. 12/747,483 dated Feb. 28, 2012.
Office Action in U.S. Appl. No. 12/747,483 dated Jun. 26, 2012.
International Search Report issued in PCT Application No. PCT/AU2004/000083, mailed Feb. 24, 2004.
International Search Report issued in PCT Application No. PCT/AU2004/000549, mailed Jul. 23, 2004.
International Search Report issued in PCT Application No. PCT/AU2004/000722, mailed Jun. 29, 2004.

International Search Report issued in PCT Application No. PCT/AU2004/001196, mailed Sep. 27, 2004.

International Search Report issued in PCT Application No. PCT/AU2006/000755, dated Aug. 30, 2006.

International Search Report issued in PCT Application No. PCT/AU2008/000367, dated May 14, 2008.

International Preliminary Report on Patentability in PCT Application No. PCT/AU2008/000367, dated May 6, 2009.

International Search report issued in PCT Application No. PCT/AU2008/001796, mailed Feb. 23, 2009.

International Search report issued in PCT Application No. PCT/AU2008/001751, mailed Feb. 18, 2009.

International Search Report issued in PCT Application No. PCT/AU2008/001891, mailed Feb. 3, 2009.

International Search Report issued in PCT Application No. PCT/AU2010/000055, mailed Mar. 18, 2010.

International Preliminary Report on Patentability and Written Opinion issued in PCT Application No. PCT/AU2010/000055 mailed Oct. 11, 2010.

Extended European Search Report issued on Dec. 4, 2008 in European Application No. 05779000.8.

Extended European Search Report issued on Nov. 7, 2008 in European Application No. 05821631.8.

Extended European Search Report issued on Mar. 12, 2009 in European Patent Application No. EP 05813335.6.

Extended European Search Report issued on Aug. 7, 2009 in European Patent Application No. EP 06774977.0.

Extended European Search Report issued on Dec. 2, 2010 in European Patent Application No. EP 08853330.2.

* cited by examiner

A: HPV-18 specific primers

B: HPV-1a specific primers

C: HPV-16 specific primers

SEQUENCE LISTING

<160> NUMBER OF SEQ ID NOS: 27

<210> SEQ ID NO 1
<211> LENGTH: 110
<212> TYPE: DNA
<213> ORGANISM: Artificial Sequence
<220> FEATURE:
<223> OTHER INFORMATION: Artificially Synthesized Peptide

<400> SEQUENCE: 1
agggaatttt ttttcgcgat gtttcggcgc gttagttcgt tgcgtatatt tcgttgcggt    60
tttttttttg gttttttcgg ttagttgcgc ggcgatttcg gggattttag                110

<210> SEQ ID NO 2
<211> LENGTH: 110
<212> TYPE: DNA
<213> ORGANISM: Artificial Sequence
<220> FEATURE:
<223> OTHER INFORMATION: Artificially Synthesized Peptide -continued

<400> SEQUENCE: 2 agggaattt tttttgtgat gttttggtgt gttagtttgt tgtgtatatt ttgttgtggt    60
tttttttttg gtttttttgg ttagttgtgt ggtgattttg gggattttag            110

<210> SEQ ID NO 3
<211> LENGTH: 40
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(40)
<223> OTHER INFORMATION: n = deoxyinosine

<400> SEQUENCE: 3 agggaattt ttttcgcnat gtttcggcgc gttagttcgt                         40

<210> SEQ ID NO 4
<211> LENGTH: 40
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(40)
<223> OTHER INFORMATION: n = deoxyinosine

<400> SEQUENCE: 4
ctaaaatccc cgaaatcgcc gcncaactaa ccgaaaaaac                        40

<210> SEQ ID NO 5
<211> LENGTH: 40
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(40)
<223> OTHER INFORMATION: n is deoxyinosine

<400> SEQUENCE: 5
aggnaatttt ttttcgcnat gtttcggcgc gttagttcgt                        40

<210> SEQ ID NO 6
<211> LENGTH: 40
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(40)
<223> OTHER INFORMATION: n is deoxyinosine

<400> SEQUENCE: 6
ctaaaatccc cgaaatcgcc ncgcaactaa ccgaaaaaac                        40

<210> SEQ ID NO 7
<211> LENGTH: 40
<212> TYPE: DNA
<213> ORGANISM: Artificial Sequence
<220> FEATURE:
<223> OTHER INFORMATION: Artificially Synthesized Peptide

```
<220> FEATURE:
<221> NAME/KEY: misc_feature
<222> LOCATION: (1)..(40)
<223> OTHER INFORMATION: n is deoxyinosine

<400> SEQUENCE: 7
aacaaaactg ctcnccagaa cactacnagc cacagcttaa                              40

<210> SEQ ID NO 8
<211> LENGTH: 40
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(40)
<223> OTHER INFORMATION: n = deoxyinosine

<400> SEQUENCE: 8
tggtgaggtt gatcngggtt tatcnattac agaacaggct                              40

<210> SEQ ID NO 9
<211> LENGTH: 40
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(40)
<223> OTHER INFORMATION: n = deoxyinosine

<400> SEQUENCE: 9
ggaggagtta gtgtcncctc agcaacctta tgctgtcntt                              40

<210> SEQ ID NO 10
<211> LENGTH: 39
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(39)
<223> OTHER INFORMATION: n = deoxyinosine

<400> SEQUENCE: 10
gcacagtggg cacacnatgt tcaaagatcn cagaaggag                               39

<210> SEQ ID NO 11
<211> LENGTH: 36
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(36)
<223> OTHER INFORMATION: n = deoxyinosine

<400> SEQUENCE: 11
ccagctggac aagcagaacc ngacagagcc cattac                                  36

<210> SEQ ID NO 12
<211> LENGTH: 41
<212> TYPE: DNA
<213> ORGANISM: Artificial Sequence
<220> FEATURE:
<223> OTHER INFORMATION: Artificially Synthesized Peptide
```

```
<220> FEATURE:
<221> NAME/KEY: misc_feature
<222> LOCATION: (1)..(41)
<223> OTHER INFORMATION: n = deoxyinosine

<400> SEQUENCE: 12
ccaaagtacg aatgtctacn tgtgtgcttt gtacncacaa c                    41

<210> SEQ ID NO 13
<211> LENGTH: 42
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(42)
<223> OTHER INFORMATION: n = deoxyinosine

<400> SEQUENCE: 13
gctgcaaccg agcacnacag gaacgactcc aacgacncag ag                   42

<210> SEQ ID NO 14
<211> LENGTH: 40
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(40)
<223> OTHER INFORMATION: n = deoxyinosine

<400> SEQUENCE: 14
acaacattgt gtgacnttgt ggttcggctc ntcgggctgg                      40

<210> SEQ ID NO 15
<211> LENGTH: 41
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(41)
<223> OTHER INFORMATION: n = deoxyinosine

<400> SEQUENCE: 15
aaattccngt tgaccttcta tgtcacnagc aattaagcga c                    41

<210> SEQ ID NO 16
<211> LENGTH: 40
<212> TYPE: DNA
<213> ORGANISM: Artificial Sequence
<220> FEATURE:
<223> OTHER INFORMATION: Artificially Synthesized Peptide

<400> SEQUENCE: 16
agggaatttt ttttcgcgat gtttcggcgc gttagttcgt                      40

<210> SEQ ID NO 17
<211> LENGTH: 40
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(40)
<223> OTHER INFORMATION: n = deoxyinosine
```

```
<400> SEQUENCE: 17 agggaattttt ttttcgngat gtttcggcgc gttagttcgt                          40

<210> SEQ ID NO 18
<211> LENGTH: 40
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(40)
<223> OTHER INFORMATION: n = deoxyinosine

<400> SEQUENCE: 18 agggaattttt ttttcgcgnt gtttcggcgc gttagttcgt                          40

<210> SEQ ID NO 19
<211> LENGTH: 40
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(40)
<223> OTHER INFORMATION: n = deoxyinosine

<400> SEQUENCE: 19 agggaattttt ttttcgcgan gtttcggcgc gttagttcgt                          40

<210> SEQ ID NO 20
<211> LENGTH: 40
<212> TYPE: DNA
<213> ORGANISM: Artificial Sequence
<220> FEATURE:
<223> OTHER INFORMATION: Artificially Synthesized Peptide

<400> SEQUENCE: 20
ctaaaatccc cgaaatcgcc gcgcaactaa ccgaaaaaac                           40

<210> SEQ ID NO 21
<211> LENGTH: 40
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(40)
<223> OTHER INFORMATION: n = deoxyinosine

<400> SEQUENCE: 21
ctaaaatccc cgaaatngcc gcgcaactaa ccgaaaaaac                           40

<210> SEQ ID NO 22
<211> LENGTH: 40
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(40)
<223> OTHER INFORMATION: n is deoxyinosine

<400> SEQUENCE: 22
ctaaaatccc cgaantcgcc gcgcaactaa ccgaaaaaac                           40
```

```
<210> SEQ ID NO 23
<211> LENGTH: 40
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(40)
<223> OTHER INFORMATION: n = deoxyinosine

<400> SEQUENCE: 23
ctaaaatccc cgaaancgcc gcgcaactaa ccgaaaaaac                                40

<210> SEQ ID NO 24
<211> LENGTH: 44
<212> TYPE: DNA
<213> ORGANISM: Artificial Sequence
<220> FEATURE:
<223> OTHER INFORMATION: Artificially Synthesized Peptide

<400> SEQUENCE: 24 agggaattttt ttttcgrcrg raurgtttcg gcgcgttagt tcgt                          44

<210> SEQ ID NO 25
<211> LENGTH: 44
<212> TYPE: DNA
<213> ORGANISM: Artificial Sequence
<220> FEATURE:
<223> OTHER INFORMATION: Artificially Synthesized Peptide

<400> SEQUENCE: 25
ctaaaatccc cgaaaurcrg rcrcgcgcaa ctaaccgaaa aaac                           44

<210> SEQ ID NO 26
<211> LENGTH: 43
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(43)
<223> OTHER INFORMATION: n = deoxyinosine

<400> SEQUENCE: 26 agggaattttt ttttcgcnnn gatgtttcgg cgcgttagtt cgt                           43

<210> SEQ ID NO 27
<211> LENGTH: 44
<212> TYPE: DNA
<213> ORGANISM: Artificial Sequence
<220> FEATURE:
<223> OTHER INFORMATION: Artificially Synthesized Peptide
<220> FEATURE:
<221> NAME/KEY: misc_feature
<222> LOCATION: (1)..(44)
<223> OTHER INFORMATION: n = deoxyinosine

<400> SEQUENCE: 27
ctaaaatccc cgaaatcggc cnnngcgcaa ctaaccgaaa aaac                           44
```

US 8,431,347 B2

ISOTHERMAL STRAND DISPLACEMENT AMPLIFICATION USING PRIMERS CONTAINING A NON-REGULAR BASE

This application is the U.S. National Phase under 35 U.S.C. §371 of International Application No. PCT/AU2006/000698, filed May 25, 2006, which claims priority to the U.S. Provisional Patent Application No. 60/685,697, filed May 26, 2005. The International Application was published in English under PCT Article 21(2) on Nov. 30, 2006.

TECHNICAL FIELD

The present invention relates to methods for amplifying nucleic acid molecules without thermal cycling.

BACKGROUND ART

The most widely used method for amplification of specific sequences from within a population of nucleic acid sequences is that of polymerase chain reaction (PCR) (Dieffenbach C and Dveksler G eds. PCR Primer: A Laboratory Manual. Cold Spring Harbor Press, Plainview N.Y.). In this amplification method, oligonucleotides, generally 15 to 30 nucleotides in length on complementary strands and at either end of the region to be amplified, are used to prime DNA synthesis on denatured single-stranded DNA templates. Successive cycles of denaturation, primer hybridisation and DNA strand synthesis using thermostable DNA polymerases allows exponential amplification of the sequences between the primers. RNA sequences can be amplified by first copying using reverse transcriptase to produce a cDNA copy. Amplified DNA fragments can be detected by a variety of means including gel electrophoresis, hybridisation with labelled probes, use of tagged primers that allow subsequent identification (e.g. by an enzyme linked assay), use of fluorescently-tagged primers that give rise to a signal upon hybridisation with the target DNA (e.g. Beacon and TaqMan systems).

One disadvantage of PCR is the need of a thermocycler to heat and cool the amplification mixture to denature the DNA. This, amplification cannot be carried out in primitive sites or operated easily outside of a laboratory environment.

As well as PCR, a variety of other techniques have been developed for detection and amplification of specific sequences. One example is the ligase chain reaction (Barany F Genetic disease detection and DNA amplification using cloned thermostable ligase. Proc. Natl. Acad. Sci. USA 88:189-193 (1991)).

In addition to conventional methods of DNA amplification that rely on the thermal denaturation of the target during the amplification reaction, a number of methods have been described that do not require template denaturation during the amplification reaction and are thus termed isothermal amplification technologies.

Isothermal amplification was first described in 1992 (Walker G T, Little M C, Nadeau J G and Shank D. Isothermal in vitro amplification of DNA by a restriction enzyme/DNA polymerase system. PNAS 89: 392-396 (1992) and termed Strand Displacement Amplification (SDA). Since then, a number of other isothermal amplification technologies have been described including Transcription Mediated Amplification (TMA) and Nucleic Acid Sequence Based Amplification (NASBA) that use an RNA polymerase to copy RNA sequences but not corresponding genomic DNA (Guatelli J C, Whitfield K M, Kwoh D Y, Barringer K J, Richmann D D and Gingeras T R. Isothermal, in vitro amplification of nucleic acids by a multienzyme reaction modeled after retroviral replication. PNAS 87: 1874-1878 (1990): Kievits T, van Gemen B, van Strijp D, Schukkink R, Dircks M, Adriaanse H, Malek L, Sooknanan R, Lens P. NASBA isothermal enzymatic in vitro nucleic acid amplification optimized for the diagnosis of HIV-1 infection. J Virol Methods. 1991 December; 35(3):273-86).

Other DNA-based isothermal techniques include Rolling Circle Amplification (RCA) in which a DNA polymerase extends a primer directed to a circular template (Fire A and Xu SQ. Rolling replication of short circles. PNAS 92: 4641-4645 (1995), Ramification Amplification (RAM) that uses a circular probe for target detection (Zhang W, Cohenford M, Lentrichia B, Isenberg H D, Simson E, Li H, Yi J, Zhang D Y. Detection of *Chlamydia trachomatis* by isothermal ramification amplification method: a feasibility study. J Clin Microbiol. 2002 January; 40(1):128-32.) and more recently, Helicase-Dependent isothermal DNA amplification (HDA), that uses a helicase enzyme to unwind the DNA strands instead of heat (Vincent M, Xu Y, Kong H. Helicase-dependent isothermal DNA amplification. EMBO Rep. 2004 August; 5(8):795-800.)

Recently, isothermal methods of DNA amplification have been described (Walker G T, Little M C, Nadeau J G and Shank D. Isothermal in vitro amplification of DNA by a restriction enzyme/DNA polymerase system. PNAS 89: 392-396 (1992). Traditional amplification techniques rely on continuing cycles of denaturation and renaturation of the target molecules at each cycle of the amplification reaction. Heat treatment of DNA results in a certain degree of shearing of DNA molecules, thus when DNA is limiting such as in the isolation of DNA from a small number of cells from a developing blastocyst, or particularly in cases when the DNA is already in a fragmented form, such as in tissue sections, paraffin blocks and ancient DNA samples, this heating-cooling cycle could further damage the DNA and result in loss of amplification signals. Isothermal methods do not rely on the continuing denaturation of the template DNA to produce single stranded molecules to serve as templates from further amplification, but rely on enzymatic nicking of DNA molecules by specific restriction endonucleases at a constant temperature.

The technique termed Strand Displacement Amplification (SDA) relies on the ability of certain restriction enzymes to nick the unmodified strand of hemi-modified DNA and the ability of a 5'-3' exonuclease-deficient polymerase to extend and displace the downstream strand. Exponential amplification is then achieved by coupling sense and antisense reactions in which strand displacement from the sense reaction serves as a template for the antisense reaction (Walker G T, Little M C, Nadeau J G and Shank D. Isothermal in vitro amplification of DNA by a restriction enzyme/DNA polymerase system. PNAS 89: 392-396 (1992). Such techniques have been used for the successful amplification of *Mycobacterium tuberculosis* (Walker G T, Little M C, Nadeau J G and Shank D. Isothermal in vitro amplification of DNA by a restriction enzyme/DNA polymerase system. PNAS 89: 392-396 (1992), HIV-1, Hepatitis C and HPV-16 Nuovo G. J., 2000), *Chlamydia trachomatis* (Spears P A, Linn P, Woodard D L and Walker G T. Simultaneous Strand Displacement Amplification and Fluorescence Polarization Detection of *Chlamydia trachomatis*. Anal. Biochem. 247: 130-137 (1997).

The use of SDA to date has depended on modified phosphorthioate nucleotides in order to produce a hemi-phosphorthioate DNA duplex that on the modified strand would be resistant to enzyme cleavage, resulting in enzymic nicking instead of digestion to drive the displacement reaction.

Recently, however, several "nickase" enzyme have been engineered. These enzymes do not cut DNA in the traditional manner but produce a nick on one of the DNA strands. "Nickase" enzymes include N.Alw1 (Xu Y, Lunnen K D and Kong H. Engineering a nicking endonuclease N.Alw1 by domain swapping. PNAS 98: 12990-12995 (2001), N.BstNB1 (Morgan R D, Calvet C, Demeter M, Agra R, Kong H. Characterization of the specific DNA nicking activity of restriction endonuclease N.BstNBI. Biol. Chem. 2000 November; 381 (11):1123-5.) and Mly1 (Besnier C E, Kong H. Converting MlyI endonuclease into a nicking enzyme by changing its oligomerization state. EMBO Rep. 2001 September; 2(9): 782-6. Epub 2001 Aug. 23). The use of such enzymes would thus simplify the SDA procedure.

In addition, SDA has been improved by the use of a combination of a heat stable restriction enzyme (Ava1) and Heat stable Exo-polymerase (Bst polymerase). This combination has been shown to increase amplification efficiency of the reaction from a $10^8$ fold amplification to $10^{10}$ fold amplification so that it is possible using this technique to amplify unique single copy molecules. The resultant amplification factor using the heat stable polymerase/enzyme combination is in the order of $10^9$ (Milla M. A., Spears P., A., Pearson R. E. and Walker G. T. Use of the Restriction Enzyme Ava1 and Exo-Bst Polymerase in Strand Displacement Amplification Biotechniques 1997 24:392-396.)

To date, all isothermal DNA amplification techniques require the initial double stranded template DNA molecule to be denatured prior to the initiation of amplification. In addition, amplification is only initiated once from each priming event.

The present inventors have now developed amplification methods which utilise enzymes and primers and do not require repeated temperature cycling.

DISCLOSURE OF INVENTION

In a first aspect, the present invention provides a method for isothermal DNA amplification comprising:
providing to the DNA to be amplified an amplification mix comprising:
a first primer at least partially complementary to a region of DNA and containing a non-regular base,
a second primer at least partially complementary to a region of DNA and containing a non-regular base,
a DNA polymerase,
an enzyme capable of strand displacement,
an enzyme that recognises a non-regular base in double-stranded DNA and causes a nick or excises a base in one DNA strand at or near the non-regular base; and
amplifying the DNA substantially without thermal cycling.

Optionally, the DNA can be denatured prior to, during, or at after addition of the amplification mix.

Preferably, the first primer is at least partially complementary to a region of a first strand of DNA, and the second primer is at least partially complementary to a region of DNA of the second strand of DNA.

The first and second primers can be oligonucleotides, oligonucleotide analogues, oligonucleotides of chimeric nature such as PNA/oligonucleotides or INA/oligonucleotides. Preferably, the primers are deoxyoligonucleotides.

Preferably, the oligonucleotide analogue is selected from intercalating nucleic acid (INA), peptide nucleic acid (PNA), hexitol nucleic acid (HNA), MNA, altritol nucleic acid (ANA), locked nucleic acid (LNA), cyclohexanyl nucleic acid (CAN), CeNA, TNA, (2'-NH)-TNA, nucleic acid based conjugates, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo [3.2.1]-DNA, Bicyclo[4.3.0]amide-DNA, β-D-Ribopyranosyl-NA, α-L-Lyxopyranosyl-NA, 2'—R-RNA, 2'-OR-RNA, α-L-RNA, and β-D-RNA, and mixtures thereof and hybrids thereof, as well as phosphorous atom modifications thereof, such as but not limited to phosphorothioates, methyl phospholates, phosphoramidites, phosphorodithiates, phosphoroselenoates, phosphotriesters and phosphoboranoates. In addition non-phosphorous containing compounds may be used for linking to nucleotides such as but not limited to methyliminomethyl, formacetate, thioformacetate and linking groups comprising amides. In particular nucleic acids and nucleic acid analogues may comprise one or more intercalator pseudonucleotides.

By INA is meant an intercalating nucleic acid in accordance with the teaching of WO 03/051901, WO 03/052132, WO 03/052133 and WO 03/052134 (Unest NS, assigned to Human Genetic Signatures Pty Ltd) incorporated herein by reference. An INA is an oligonucleotide or oligonucleotide analogue comprising one or more intercalator pseudonucleotide (IPN) molecules.

When a primer having the non-regular base binds to DNA it forms a site recognised by the enzyme.

The non-regular base (ie non-regular DNA base) is defined herein as a chemical entity other than adenine (A), thymine (T), guanine (G) and cytosine (C) capable of being inserted in a DNA backbone. Examples of non-regular bases include, but not limited, to deoxyinosine, 8 deoxyguanine, hydroxyuracil, 5-methyl-dC, 5 hydroxyuridine, 5 bromo-dU Inosine with C, ribonucleotides, and uracil. More preferably, the non-regular base is deoxyinosine.

It will be appreciated, however, that the non-regular base does not necessarily need to have the structure of a nucleotide.

The primers can have one or more non-regular bases. In some situations, two or more non-regular bases can improve the amplification process. The non-regular bases can be positioned close or spaced apart by at least several regular bases.

The DNA polymerase can be any suitable polymerase such as Taq polymerase Stoffel fragment, Taq polymerase, Advantage DNA polymerase, AmpliTaq, Amplitaq Gold, Titanium Taq polymerase, KlenTaq DNA polymerase, Platinum Taq polymersae, Accuprime Taq polymerase, Pfu polymerase, Pfu polymerase turbo, Vent polymerase, Vent exo-polymerase, Pwo polymerase, 9° N, DNA polymerase, Therminator, Pfx DNA polymerase, Expand DNA polymerase, rTth DNA polymerase, DyNAzyme™ EXT Polymerase, Klenow fragment, DNA polymerase 1, DNA polymerase, T7 polymerase, Sequenase™, T4 DNA polymerase, Bst B polymerase, phi-29 DNA polymerase and DNA polymerase Beta.

The strand displacement enzyme can be any suitable enzyme such as Helicases, AP endonucleases, mismatch repair enzymes capable of stand displacement or genetically (or otherwise) modified enzyme capable of stand displacement.

In a preferred form, the DNA polymerase also has strand displacement capability. The DNA polymerase can be any suitable polymerase having strand displacement capability. Examples include, but not limited to, Klenow exo- (New England Biolabs (NEB) catalogue number MO212S), Bst DNA polymerase large., fragment (NEB catalogue number MO275S), Vent exo- (NEB catalogue number MO257S), Deep Vent exo-(NEB catalogue number MO259S), M-MuLV reverse transcriptase (NEB catalogue number MO253S), 9° Nm DNA polymerase (NEB catalogue number MO260S) and Phi29 DNA polymerase (NEB catalogue number MO269S) ThermoPhi™ (Prokaria ehf). Preferably, the DNA polymerase is Klenow Exo-.

Preferably, the DNA polymerase is exonuclease deficient.

The enzyme can be any suitable enzyme that is capable of recognising non-regular base in double stranded DNA and can cause a nick or excise a base at or near the site of the non-regular base. Examples include, but not limited to, Endonuclease V (deoxyinosine 3' endonuclease) (NEB catalogue number M0305S), Fpg (NEB catalogue number M0240S), hOGG1 (NEB catalogue number M0241S), RNase H (NEB catalogue number M0297S), APE1 (NEB catalogue number M0282S), Endonuclease III (NEB catalogue number MO268S), Endonuclease IV (NEB catalogue number M0304S), Endonuclease VIII (NEB catalogue number MO299S), T7 Endonuclease I (NEB catalogue number M0302S), USER Enzyme (NEB catalogue number M5505S), McrBC (NEB catalogue number M0272S) and Uracil DNA glycosylase (NEB catalogue number M0280S). Preferably, the enzyme is Endonuclease V.

It will be appreciated that other suitable enzymes can be made or obtained that recognise a non-regular base in double stranded DNA and act as required by nicking or causing base removal in the method according to the present invention.

The additives required for DNA amplification include nucleotides, buffers or diluents such as magnesium or manganese ions, co-factors, etc known to the art.

The amplification mix can also contain nucleotides, buffers or diluents such as magnesium or manganese ions, co-factors and suitable additives such as single stranded binding proteins such as T4gp32 or RecA.

Amplification can be carried out at any suitable temperature where the enzymes have desired activity. Typically, the temperature can be about 20° C. to about 75° C., about 25° C. to 60° C., or about 30° C. to 45° C. For the enzymes used in the current study, about 42° C. has been found to be particularly suitable. It will be appreciated that other temperatures, either higher or lower, can be used and would include ambient or room temperature. Importantly, the present invention does not require thermal cycling to amplify nucleic acids.

In one preferred from, the DNA is pre-treated with a modifying agent which modifies cytosine bases but does not modify 5'-methyl-cytosine bases under conditions to form single stranded modified DNA. Preferably, the modifying agent is selected from bisulphite, acetate or citrate and treatment does not result in substantial DNA fragmentation. More preferably, the agent is sodium bisulphite, a reagent, which in the presence of water, modifies cytosine into uracil.

Sodium bisulphite.($NaHSO_3$) reacts readily with the 5,6-double bond of cytosine to form a sulfonated cytosine reaction intermediate which is susceptible to deamination, and in the presence of water gives rise to a uracil sulfite. If necessary, the sulfite group can be removed under mild alkaline conditions, resulting in the formation of uracil. Thus, potentially all cytosines will be converted to uracils. Any methylated cytosines, however, cannot be converted by the modifying reagent due to protection by methylation.

Preferred methods for bisulphite treatment of nucleic acid can be found in WO 2004/096825 in the name of Human Genetic Signatures Pty Ltd (Australia), incorporated herein by reference.

If both strands of the treated DNA need to be amplified in the same amplification reaction, then four primers can be used (ie two primers for each of the modified strands of DNA).

In a second aspect, the present invention provides a kit for isothermal DNA amplification comprising:
  a DNA polymerase;
  an enzyme capable of strand displacement; and
  an enzyme that recognises a non-regular base in double stranded DNA and causes a nick or excises a base in one DNA strand at or near the site of the non-regular base.

Preferably the kit further comprises:
  additives required for DNA amplification.
Preferably the kit further comprises:
  instructions to use the kit.

In a preferred form, the DNA polymerase and enzyme capable of strand displacement are the same enzyme.

In a third aspect, the present invention provides a primer for isothermal DNA amplification containing at least one internal non-regular base and when bound to a region of DNA forms a site recognised by an enzyme capable of causing a nick or excising a base in one DNA strand at or near the site of the non-regular base.

Preferably, the non-regular base is a chemical entity other than adenine (A), thymine (T), guanine (G) and cytosine (C) capable of being inserted in a DNA backbone. More preferably, the non-regular base is selected from the group consisting of deoxyinosine, 8 deoxyguanine, 5-methylCytosine, hydroxyuracil, ribonucleotides, and uracil. More preferably, the non-regular base is deoxyinosine.

In a fourth aspect, the present invention provides use of the kit according to the second aspect of the present invention for DNA amplification substantially without thermal cycling.

In a fifth aspect, the present invention provides use of a primer according to the fourth aspect of the present invention for DNA amplification substantially without thermal cycling.

In a sixth aspect, the present invention provides use of a DNA polymerase having strand displacement capability for DNA amplification substantially without thermal cycling.

In a seventh aspect, the present invention provides use of an enzyme that recognises a non-regular base in double stranded DNA and causes a nick or excises a base in one DNA strand at or near the site of the non-regular base for DNA amplification substantially without thermal cycling.

In a eighth aspect, the present invention provides use of a DNA polymerase having strand displacement capability and an enzyme that recognises a non-regular base in double stranded DNA and causes a nick or excises a base in one DNA strand at or near the site of the non-regular base for DNA amplification substantially without thermal cycling.

The amplification method of the present invention can be used as a replacement for PCR or other known DNA amplification processes. Uses include, but not limited to, detection of disease, amplifying desired genes or segments of DNA or RNA, SNP detection, real time amplification procedures, amplifying bisulphite treated DNA, whole genome amplification methods, adjunct to cloning methods, in situ amplification of DNA on cytological specimens, such as detection of microbes in sections or smears, detection of microbes in food contamination, amplification of breakpoints in chromosomes such as BCR-ABL translocations in various cancers, amplification of sequences inserted into chromosomes that may be oncogenic and predictive of disease progression, such as HPV fragment insertion, detection of methylated versus unmethylated sequences in normal versus cancerous cells, and in in situ tests for methylation changes in IVF tests for the normalcy of blastocyst development.

A distinct advantage of the present invention is that it can be carried out directly on double stranded DNA. The invention can also used for RNA by carrying out reverse transcription of the RNA prior to isothermal amplification. Furthermore, the present invention does not require heating or cooling for amplification. It is contemplated that the method according to the present invention can be carried 'in the field' i.e. at room or ambient temperature without the need for powered laboratory equipment.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a Context for the present invention. It is not to be taken as an admission that any or all of these Matters form part of the prior art base or were common general knowledge in the field relevant to the present invention as it existed prior to development of the present invention.

In order that the present invention may be more clearly understood, preferred embodiments will be described with reference to the following drawings and examples.

MODE(S) FOR CARRYING OUT THE INVENTION

Materials and Methods

Non-Regular Bases

A non-regular base is defined herein as a chemical entity other than adenine (A), thymine (T), guanine (G) and cytosine (C) capable of being inserted in a DNA backbone. Examples of non-regular bases include, but not limited, to deoxyinosine, 8 deokyguanine or hydroxyuracil, 5-methyl-dC, 5 bromo-dU Inosine with C ribonucleotides, and uracil.

The non-regular base deoxyinosine has been found to be useful by the present invention.

It should be noted that the non-regular base does not necessarily need to have the structure of a nucleotide to function in the present invention.

Primers

Primers can be synthesised using any commercially available DNA synthesis service or in-house DNA synthesisers. The non-regular bases can be incorporated into the primer at any position using standard phosphoamidite synthesis technology.

Enzymes

Several modes are available for carrying out this invention.

I. Oligonucleotides containing deoxyinosine, a non-regular base which is recognised by the enzyme Endonuclease V II. Oligonucleotides containing 8 deoxyguanine or hydroxyuracil, non-regular bases which are recognised by the enzyme Fpg.

III. Oligonucleotides containing 8 deoxyguanine or hydroxyuracil, non-regular bases which are recognised by the enzyme hOGG1

IV. Oligonucleotides containing ribonucleotides, non-regular bases which are recognised by the enzyme RNase H V. Oligonucleotides containing uracil, a non-regular base which is recognised by the enzyme Uracil DNA glycosylase or USER enzyme.

VI. Oligonucleotides containing 5-methylCytosine, non-regular bases which are recognised by the enzyme McrBC.

Enzymes capable of strand displacement include Klenow exo-, Bst DNA polymerase large fragment, Vent exo-, Deep Vent exo-, M-MuLV reverse transcriptase, 9° Nm DNA polymerase and Phi29 DNA polymerase.

The DNA polymerase can be any suitable polymerase having strand displacement capability. Examples include, but not limited to, Klenow exo- (New England Biolabs (NEB) catalogue number M0212S), Bst DNA polymerase large fragment (NEB catalogue number M0275S), Vent exo- (NEB catalogue number M0257S), Deep Vent exo-(NEB catalogue number M0259S), M-MuLV reverse transcriptase (NEB catalogue number M0253S), 9° Nm DNA polymerase (NEB catalogue number M0260S) and Phi29 DNA polymerase (NEB catalogue number M0269S) ThermoPhi™ (Prokaria ehf). Preferably, the DNA polymerase is Klenow Exo-.

Amplification Mix

The non-regular base in primers was N=deoxyinosine.

DNA polymerase capable of strand displacement was Endonuclease V

Enzyme that recognises a non-regular base in double stranded DNA was Klenow Exo- 50 ng of primers 500 μM dNTPs, 1 mM MgCl$_2$, 9 μl of X1 Stoffel buffer (Perkin Elmer-Applied Biosystems, Foster City, USA) in a reaction vessel.

Amplification

Figure 1:
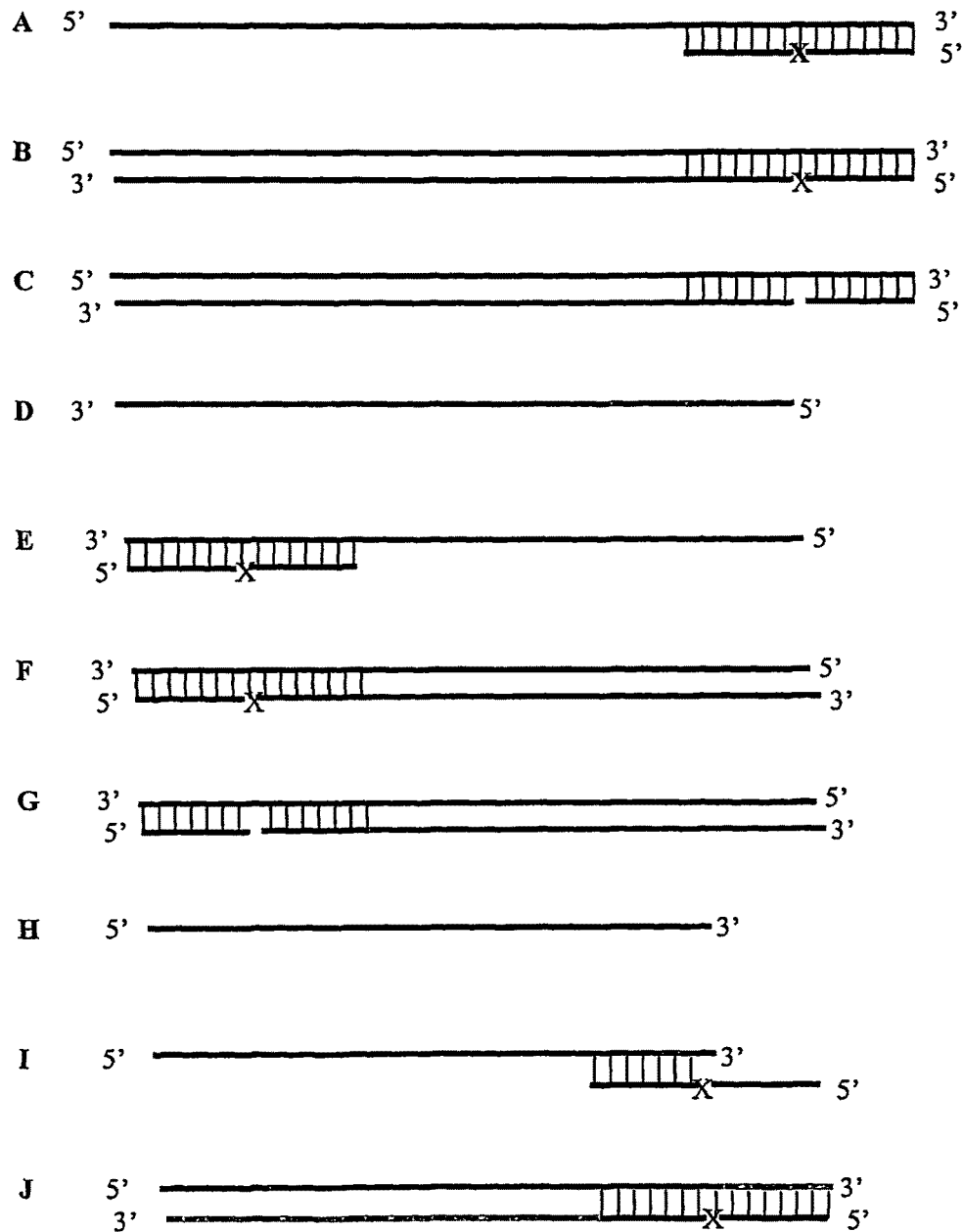
FIG. 1 shows a schematic representation of a nucleic acid amplification method according to the present invention.

Amplification according to the present invention occurs in the following manner (see FIG. 1):

the first primer binds to one strand of DNA (A), the DNA polymerase extends the first primer forming a double stranded molecule having a first newly synthesised strand containing a non-regular base (B), the nicking enzyme causes a nick or base excision at or near the non-regular base of the extended DNA (C);

the strand displacing enzyme or DNA polymerase capable of strand displacement displaces the first newly synthesised strand (D), the second primer binds to the displaced first newly synthesised strand (E), the DNA polymerase extends the second primer forming a double stranded molecule having a second newly synthesised strand containing a non-regular base (F), the nicking enzyme causes a nick or base excision at or near the non-regular base of the extended DNA (G), the strand displacing enzyme or DNA polymerase capable of strand displacement displaces the second newly synthesised strand (H), the first primer binds to the displaced second newly synthesised strand (I), and the process continues forming repeated newly synthesised strands of DNA (J).

The polymerase should copy the first primer in a 5'-3' direction as if this does not occur the reaction would stop after the third cycle of amplification as the nick site will be lost preventing further amplification. The above reaction will then continue cycling with repeated rounds of nicking, extension and displacement. The primer is usually regenerated by the polymerase to allow successive rounds of amplification.

Results

Specificity of Isothermal Amplification

In order to demonstrate the specificity of the present invention, amplification reaction was parried out on two artificial DNA molecules (target and non-target).

Target
(SEQ ID NO 1)
5' AGGGAATTTTTTTTCGCGATGTTTCGGCGCGTTAGTTCGTTGCGTAT
ATTTCGTTGCGGTTTTTTTTTTGGTTTTTTCGGTTAGTTGCGCGGCGATT
TCGGGGATTTTAG 3'

Non-target
(SEQ ID NO 2)
5' AGGGAATTTTTTTTTGTGATGTTTTGGTGTGTTAGTTTGTTGTGTAT
ATTTTGTTGTGGTTTTTTTTTTGGTTTTTTTGGTTAGTTGTGTGGTGATT
TTGGGGATTTTAG 3'

The difference between the two oligonucleotides was that in the non-target oligonucleotide all CpG doublets were replaced by TpG doublets.

Isothermal amplification was carried out using the following primer set directed to the detection of target DNA sequences;

Primer#1
(SEQ ID NO 3)
5' AGGGAATTTTTTTTCGCNATGTTTCGGCGCGTTAGTTCGT 3'

Primer#2
(SEQ ID NO 4)
5' CTAAAATCCCCGAAATCGCCGCNCAACTAACCGAAAAAAC 3' non-regular base was N=deoxyinosine.

Primers were synthesised using standard phosphoamidite chemistry.

Amplification was carried out under the following conditions:

50 ng of each of the above oligonucleotide primers, 500 μM dNTPs, 1 mM MgCl$_2$, 0.5U Endonuclease V, 2U Klenow Exo- in 9 μl of X1 Stoffel buffer (Perkin Elmer-Applied Biosystems, Foster City, USA).

Eight pmoles of both target and non-target oligonucleotides were diluted from $10^2$ to $10^{-4}$. One μl of the diluted DNA was then added to the above reaction mixture and incubated for 2 hours at 42° C.

Ten μl of the amplified product were mixed with 10 μl of water and the amplification products resolved on a E-Gel 48 4% agarose (HR) gel (Invitrogen Cat#G8080-04) and the gel run using the Powerbase™. Markers were the E-gel low range quantitative DNA ladder (Invitrogen cat#12373-031. Gels were visualised under UV irradiation using the Kodak UVI-doc EDAS 290 system.

Figure 2:
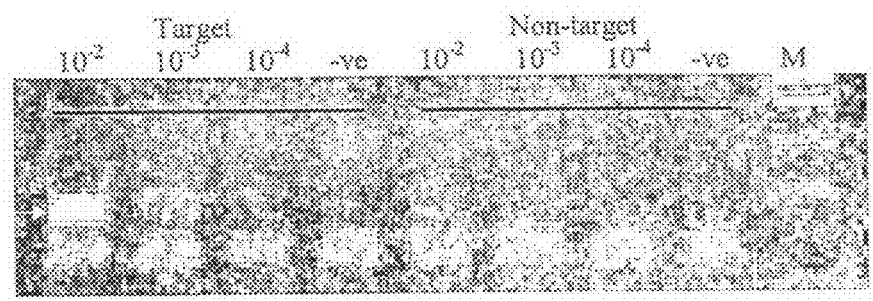
FIG. 2 shows an agarose gel analysis of the results of amplification of target sequences using a method according to the present invention.

FIG. 2 shows 4% agarose gel analysis of the amplification products produced after 2 hours incubation at 42° C. using a synthetic bisulphite methylated target sequences and a synthetic bisulphite unmethylated non-target sequences. The results demonstrate the specificity of the isothermal amplification reaction. Two synthetic 110 by oligonucleotides were synthesised (see below). Isothermal amplification was carried out using oligonucleotides containing a single internal inosine (I) base designed to be specific for the amplification of target synthetic bisulphite methylated DNA sequences. As can be seen, the reaction was specific for the amplification of target DNA molecules. No bands can be seen from the non-target even when an excess of non-target DNA was present. The reaction was specific for the detection of methylated sequences and did not amplify unmethylated sequences even when the template was in high abundance. Thus even at relatively low temperatures (42° C.) it was possible to discriminate between two sequences that are relatively similar.

Efficiency of Isothermal Amplification

In order to determine the efficiency of amplification, serially diluted target DNA was amplified by a method according to the present invention.

Figure 3:
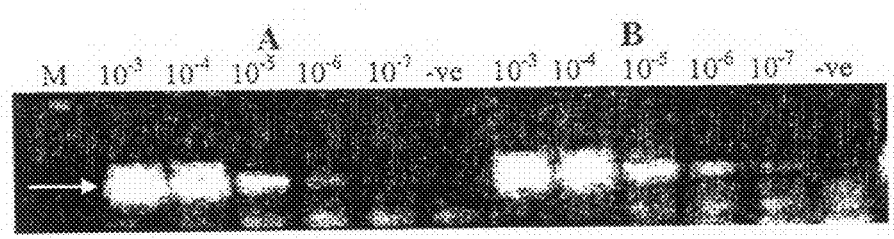
FIG. 3 shows an agarose gel analysis of the results of amplification of target sequences using a method according to the present invention.

FIG. 3 shows 4% agarose gel analysis of the amplification products produced after 4 hours incubation at 42° C. The arrow indicates the correct amplification product. The doublet in FIG. 3A is a result of full length amplification products that contain intact primer sequences and strand displaced products that contain primer sequences 5' of the inosine insertion.

Set A contained the following oligonucleotide primers

Primer#1
(SEQ ID NO 5)
5' AGGNAATTTTTTTCGCNATGTTTCGGCGCGTTAGTTCGT 3'

Primer#2
(SEQ ID NO 4)
5' CTAAAATCCCCGAAATCGCCGCNCAACTAACCGAAAAAAC 3' non-regular base was N=deoxyinosine.

Set B contained the same primers but the reaction was supplemented by the addition of 1 mM DTT.

Primer#2
(SEQ ID NO 6)
5' CTAAAATCCCCGAAATCGCCNCGCAACTAACCGAAAAAAC 3' non-regular base was N=deoxyinosine.

Primers were synthesised using standard phosphoamidite chemistry.

Amplification was carried out under the following conditions:

50 ng of each of the above oligonucleotide primers, 500 μM dNTPs, 1 mM MgCl$_2$, 0.5U Endonuclease V, 2U Klenow Exo -in 9 μl of X1 Stoffel buffer (Perkin Elmer-Applied Biosystems, Foster City, USA).

The target DNA was a synthetic 110 by oligonucleotide (SEQ ID NO 1)
5' AGGGAATTTTTTTTCGCGATGTTTCGGCGCGTTAGTTCGTTGCGTAT

ATTTCGTTGCGGTTTTTTTTTTGGTTTTTTCGGTTAGTTGCGCGGCGATT

TCGGGGATTTTAG 3'

Eight pmoles of target DNA were serially diluted from $10^{-3}$ to $10^{-7}$. One µl of the diluted DNA was then added to the above reaction mixture and incubated for 4 hours at 42° C.

Ten µl of the amplified product were mixed with 10 µl of water and the amplified products resolved on a E-Gel 48 4% agarose (HR) gel (Invitrogen Cat# G8080-04) and the gel run using the Powerbase™. Markers were the E-gel low range quantitative DNA ladder (Invitrogen cat#12373-031. Gels were visualised under UV irradiation using the Kodak UVIdoc EDAS 290 system.

As can be seen from FIG. 3 the method was capable of DNA amplification from target DNA sequences using a $10^5$ dilution of the template DNA. In addition, as can be seen from FIG. 3B by adding DTT to a final concentration of 1 mM improved the amplification as compared to FIG. 3A. This means that it was possible to have multiple displacement events from the same correctly hybridised oligonucleotide, unlike conventional PCR where only one new copy can be made from each correct priming event. This means that in theory the isothermal technique according to the present invention could be even more sensitive than PCR at amplifying DNA sequences as multiple copies of the target can be made from each correct priming event.

PCR Amplification Comparison

In order to compare the efficiency of the present invention with the market amplification standard, PCR was carried out using the same primers and target DNA.

PCR was carried out using the following primers

```
Primer#1
                                          (SEQ ID NO 3)
5' AGGGAATTTTTTTTCGCNATGTTTCGGCGCGTTAGTTCGT 3'

Primer#2
                                          (SEQ ID NO 4)
5' CTAAAATCCCCGAAATCGCCGCNCAACTAACCGAAAAAAC 3'
``` non-regular base was N=deoxyinosine.

PCR reaction mixes were prepared using 100 ng of each of the above primers in X1 Promega master mix in a total reaction volume of 25 µl. Samples of PCR products were amplified in a ThermoHybaid PX2 thermal cycler under the following conditions; 25, cycles of amplification at 95° C. for 30 seconds, 50° C. for 45 seconds, 68° C. for 45 seconds.

The target DNA was a synthetic 110, by oligonucleotide:

```
                                          (SEQ ID NO 1)
5' AGGGAATTTTTTTTCGCGATGTTTCGGCGCGTTAGTTCGTTGCGTAT

ATTTCGTTGCGGTTTTTTTTTGGTTTTTTCGGTTAGTTGCGCGGCGATT

TCGGGGATTTTAG 3'
```

Eight pmoles of target DNA were serially diluted from $10^{-2}$ to $10^{-8}$. One µl of the diluted DNA was then added to the above reaction mixture.

Ten µl of the PCR derived product were mixed with 10 µl of water and the PCR products resolved on a 4% agarose gels (Invitrogen Cat# G6000-04) and the gel run using the Powerbase™: Markers were the E-gel low range quantitative DNA ladder (Invitrogen cat#12373-031. Gels were visualised under UV irradiation using the Kodak UVIdoc EDAS 290 system.

Figure 4:
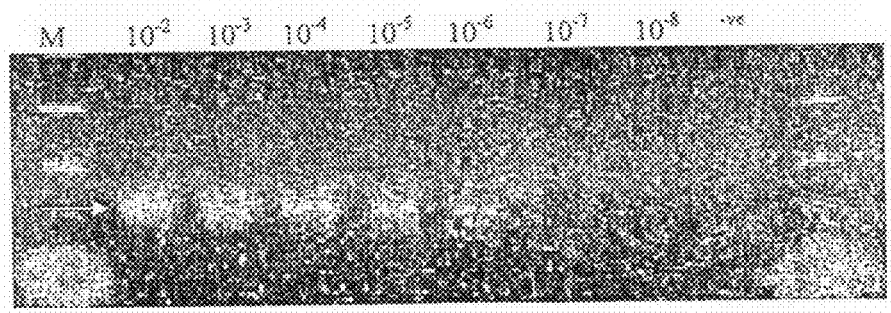
FIG. 4 shows an agarose gel analysis of a direct comparison of the isothermal method of DNA amplification with conventional Polymerase Chain Reaction (PCR).

FIG. 4 shows a direct comparison of the isothermal method of DNA amplification with conventional Polymerase Chain Reaction (PCR). Using PCR, it was just possible to see an amplified band using a $10^6$ dilution of the template DNA. The use of 25 cycles of amplification is usually sufficient to successfully amplify multi-copy targets such as 12S ribosomal DNA sequences.

From the results it can be seen that the isothermal method of DNA amplification is a rapid, sensitive and specific method for DNA amplification. The method requires no expensive cycling equipment therefore could be carried out in any routine lab or even doctors surgery.

Direct Amplification of Double Stranded DNA

Figure 5:
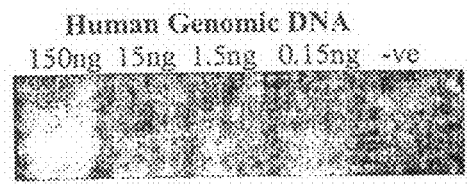
FIG. 5 shows amplification of the 12S rDNA gene from human genomic DNA.

FIG. 5 shows amplification of the 12S rDNA gene from human genomic DNA. Amplification was carried out under the following conditions:

```
50 ng of each of the oligonucleotide primers
                                          (SEQ ID NO 7)
F1 5' AACAAAACTGCTCNCCAGAACACTACNAGCCACAGCTTAA-3'
and
                                          (SEQ ID NO 8)
R1 5' TGGTGAGGTTGATCNGGGTTTATCNATTACAGAACAGGCT-3',
```

500 µM dNTPs, 1 mM $MgCl_2$ in 9 µl of X0.5 Stoffel buffer (Perkin Elmer-Applied Biosystems, Foster City, USA) and 1 µl of genomic of human genomic (Promega Cat#G147A) at concentrations of 150 ng, 15 ng, 1.5 ng and 0.15 ng. The reaction mixes were heated at 95° C. for 2 minutes then snap-chilled on ice. The reaction mixes were then supplemented with 0.5U Endonuclease V, 2U Klenow Exo- and 1 mM DTT in 10 µl of X0.5 Stoffel buffer (Perkin Elmer-Applied Biosystems, Foster City, USA).

Ten µl of the amplified product were mixed with 10 µl of water and the amplification products resolved on a E-Gel 48 4% agarose (HR) gel (Invitrogen Cat#G8080-04) and the gel run using the Powerbase™. Markers were the E-gel low range quantitative DNA ladder (Invitrogen cat#12373-031. Gels were visualised under UV irradiation using the Kodak UVIdoc EDAS 290 system.

Viral DNA Amplification

Plasmids containing full-length human papilloma virus (HPV) viral genomes HPV 1a (45021), HPV 16 (45113D) and HPV 18 (45152D) were obtained from the ATCC. Plasmids preparations were prepared as indicated by the supplier's recommendations. After plasmid purification using the Qiagen Plasmid midi kit (Cat# 12143) plasmids were linearised with Hind III (NEB Cat# R0104S) for HPV-1a and HPV-16 or with ClaI (NEB Cat# R0197S) according to the manufacturers instructions. Ten fold serial dilutions of the plasmids were prepared in sterile water to serve as templates for isothermal amplification.

Isothermal amplification was carried out using the following primer set directed to the detection of target HPV DNA sequences:

```
HPV-1a primers
Primer#1
                                          (SEQ ID NO 9)
5' GGAGGAGTTAGTGTCNCCTCAGCAACCTTATGCTGTCNTT 3'

Primer#2
                                          (SEQ ID NO 10)
5' GCACAGTGGGCACACNATGTTCAAAGATCNCAGAAGGAG 3'

HPV-16
Primer#1
                                          (SEQ ID NO 11)
5' CCAGCTGGACAAGCAGAACCNGACAGAGCCCATTAC 3'

Primer#2
                                          (SEQ ID NO 12)
5' CCAAAGTACGAATGTCTACNTGTGTGCTTTGTACNCACAAC 3'
```

```
HPV-18
Primer#1
                                             (SEQ ID NO 13)
5' GCTGCAACCGAGCACNACAGGAACGACTCCAACGACNCAGAG 3'

Primer#2
                                             (SEQ ID NO 14)
5' ACAACATTGTGTGACNTTGTGGTTCGGCTCNTCGGGCTGG 3'
``` non-regular base was N=deoxyinosine.

Primers were synthesised using standard phosphoamidite chemistry.

Amplification was carried out under the following conditions:

50 ng of each of the above oligonucleotide primers, 500 µM dNTPs, 1 mM MgCl$_2$, 0.5U Endonuclease V, 2U Klenow Exo- in 9 µl of X1 Stoffel buffer (Perkin Elmer-Applied Biosystems, Foster City, USA).

Ten-fold serial dilutions of purified plasmid DNA were prepared ranging from 100 ng/µl to 100 fg/µl. Plasmid dilutions were heated at 95° C. for 2 minutes then snap-chilled on ice until required. One µl of the diluted DNA was then added to the above reaction mixture and incubated for 4 hours at 42° C.

Figure 6:
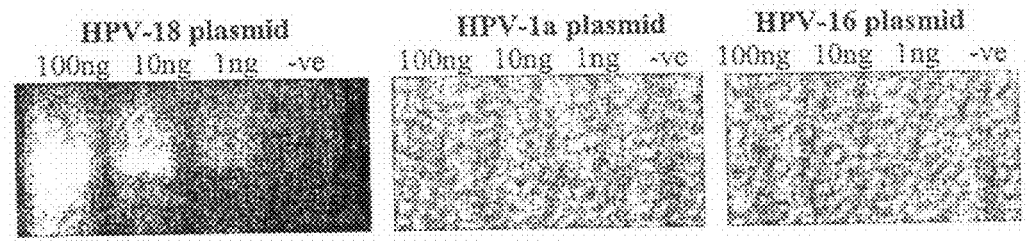
FIG. 6 shows results of isothermal amplification of various human papilloma virus (HPV) DNA.
Figure 6:
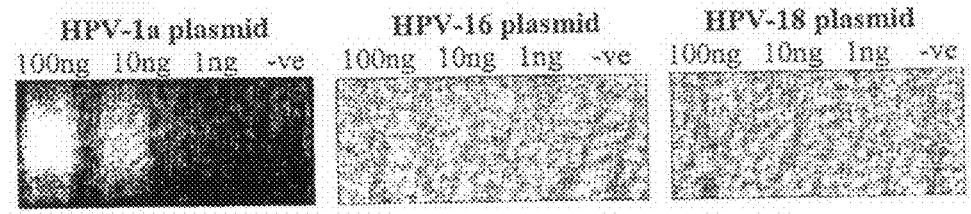
Figure 6:
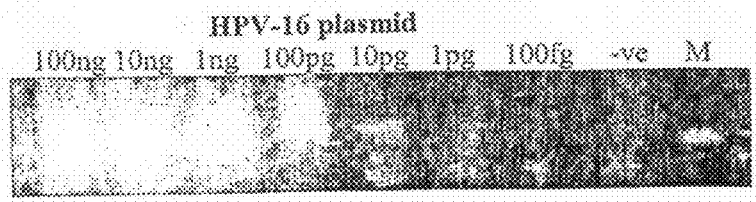

Ten µl of the amplified product were mixed with 10 µl of water and the amplification products resolved on a E-Gel 48 4% agarose (HR) gel (Invitrogen Cat# G8080-04) and the gel run using the Powerbase™, Markers (M) were the E-gel low range quantitative DNA ladder (Invitrogen cat#12373-031. Gels were visualised under UV irradiation using the Kodak UVidoc EDAS 290 system. The results are shown in FIG. 6.

The HPV 18 (45152D) was ten fold serially diluted to determine if pre-heat treatment was required for amplification using the isothermal system.

Isothermal amplification was carried out using the following primer set directed to the detection of target HPV DNA sequences:

```
HPV-18
Primer#1
                                             (SEQ ID NO 13)
5' GCTGCAACCGAGCACNACAGGAACGACTCCAACGACNCAGAG 3'

Primer#2
                                             (SEQ ID NO 15)
5' AAATTCCNGTTGACCTTCTATGTCACNAGCAATTAAGCGAC 3'
``` non-regular base was N=deoxyinosine.

Primers were synthesised using standard phosphoamidite chemistry.

Amplification was carried out under the following conditions:

50 ng of each of the above oligonucleotide primers, 500 µM dNTPs, 1 mM MgCl$_2$, 0.5U Endonuclease V, 2U Klenow Exo- in 9 µl of X1 Stoffel buffer (Perkin Elmer-Applied Biosystems, Foster City, USA).

Figure 7:
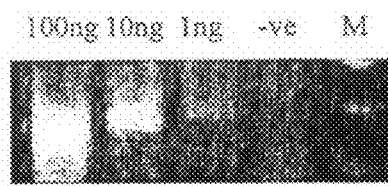
FIG. 7 shows results of isothermal amplification of human papilloma virus (HPV) DNA testing effect of NO denaturation on the reaction.

Ten-fold serial dilutions of purified plasmid DNA were prepared ranging from 100 ng/µl to 1 ng/µl. One µl of the diluted DNA without pre-denaturation was then added to the above reaction mixture and incubated for 4 hours at 42° C. Ten µl of the amplified product were mixed with 10 µl of water and the amplification products resolved on a E-Gel 48 4% agarose (HR) gel (Invitrogen Cat# G8080-04) and the gel run using the Powerbase™. Markers (M) were the E-gel low range quantitative DNA ladder (Invitrogen cat#12373-031. Gels were visualised under UV irradiation using the Kodak UVidoc EDAS 290 system. Results are shown in FIG. 7.

The results suggest that in certain instances there is no requirement for initial denaturation of double stranded DNA templates prior to isothermal amplification.

Placement of Non-Regular Base

Isothermal amplification was carried out using the following primer set directed to the detection of the following target sequence:

```
                                              (SEQ ID NO 1)
5' AGGGAATTTTTTTTCGCGATGTTTCGGCGCGTTAGTTCGTTGCGTAT
ATTTCGTTGCGGTTTTTTTTTTGGTTTTTTCGGTTAGTTGCGCGGCGATT
TCGGGGATTTTAG 3'

Wild type forward primer
                                             (SEQ ID NO 16)
  5'-AGGGAATTTTTTTTCGCGATGTTTCGGCGCGTTAGTTCGT (SEQ ID NO 3)
G 5'-AGGGAATTTTTTTTCGCNATGTTTCGGCGCGTTAGTTCGT (SEQ ID NO 17)
C 5'-AGGGAATTTTTTTTCGNGATGTTTCGGCGCGTTAGTTCGT (SEQ ID NO 18)
A 5'-AGGGAATTTTTTTTCGCGNTGTTTCGGCGCGTTAGTTCGT (SEQ ID NO 19)
T 5'-AGGGAATTTTTTTTCGCGANGTTTCGGCGCGTTAGTTCGT Wild type reverse primer
                                             (SEQ ID NO 20)
  5'-CTAAAATCCCCGAAATCGCCGCGCAACTAACCGAAAAAAC (SEQ ID NO 4)
G 5'-CTAAAATCCCCGAAATCGCCGCNCAACTAACCGAAAAAAC (SEQ ID NO 21)
C 5'-CTAAAATCCCCGAAATNGCCGCGCAACTAACCGAAAAAAC (SEQ ID NO 22)
A 5'-CTAAAATCCCCGAANTCGCCGCGCAACTAACCGAAAAAAC (SEQ ID NO 23)
T 5'-CTAAAATCCCCGAAANCGCCGCGCAACTAACCGAAAAAAC
``` non-regular base was N=deoxyinosine.

Four sets of primers were then compared to determine the effect of inosine placement in the oligonucleotide.

Primers were synthesised using standard phosphoamidite chemistry.

Amplification was carried out under the following conditions:

50 ng of each of the above oligOnucleotide primers, 500 µM dNTPs, 1 mM MgCl$_2$, 0.5U Endonuclease V, 2U Klenow Exo- in 9 µl of X1 Stoffel buffer (Perkin Elmer-Applied Biosystems, Foster City, USA).

Ten-fold serial dilutions of target DNA were prepared ranging from $10^{-2}$ dilution to $10^{-6}$. One µl of the diluted target DNA was then added to the above reaction mixture and incubated for 4 hours at 42° C.

Figure 8:
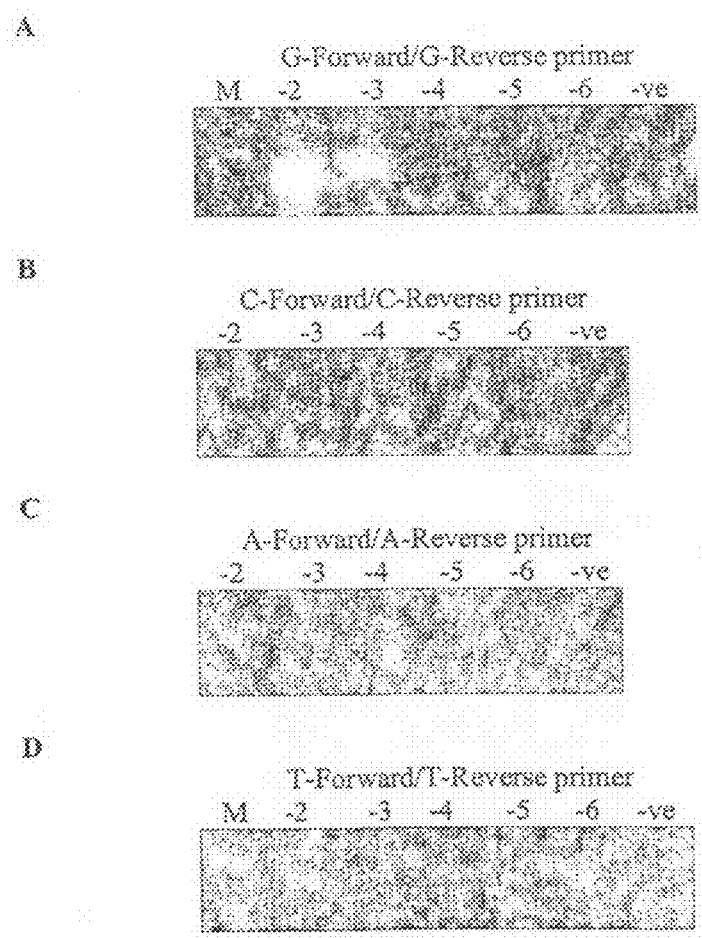
FIG. 8 shows results of isothermal amplification using various placement of non-regular bases in primers

Ten µl of the amplified product were mixed with 10 µl of water and the amplification products resolved on a E-Gel 48 4% agarose (HR) gel (Invitrogen Cat# G8080-04) and the gel run using the Powerbase™. Markers (M) were the E-gel low range quantitative DNA ladder (Invitrogen cat#12373-031. Gels were visualised under UV irradiation using the Kodak UVidoc EDAS 290 system and results shown in FIG. 8. The results for the DNA being amplified suggested that for the reaction worked more efficiently when the inosine substituted a G in the sequence. Further experiments indicated that a preferred placement of the inosine for this DNA amplification test was CI where the inosine replaced a G in a CpG dinucleotide.

Amplification Using Ribonucleotide

Isothermal amplifications were carried out using a primer set directed to the detection of the following target DNA sequences;

(SEQ ID NO 1)
5' AGGGAATTTTTTTTCGCGATGTTTCGGCGCGTTAGTTCGTTGCGTAT
ATTTCGTTGCGGTTTTTTTTTGGTTTTTTCGGTTAGTTGCGCGGCGATT
TCGGGGATTTTAG 3'

Primer#1
(SEQ ID NO 24)
5' AGGGAATTTTTTTTCGrCrGrAUrGTTTCGGCGCGTTAGTTCGT

Primer#2
(SEQ ID NO 25)
5' CTAAAATCCCCGAAAUrCrGrCrCGCGCAACTAACCGAAAAAAC non-regular base was r=ribonucleotide.

Primers were synthesised using standard phosphoamidite chemistry.

Amplification was carried out under the following conditions:

50 ng of each of the above oligonucleotide primers, 500 µM dNTPs, 1 mM MgCl$_2$, 0.1U RNaseH, 2.5U Klenow Exo- in 9 µl of X10 reaction buffer (either NEB buffer 1, Klenow Buffer or Stoffel buffer).

Ten-fold serial dilutions of target DNA were prepared ranging from $10^{-1}$ to $10^{-3}$. One µl of the diluted DNA was then added to the above reaction mixture and incubated for 4 hours at 42° C.

Figure 9:
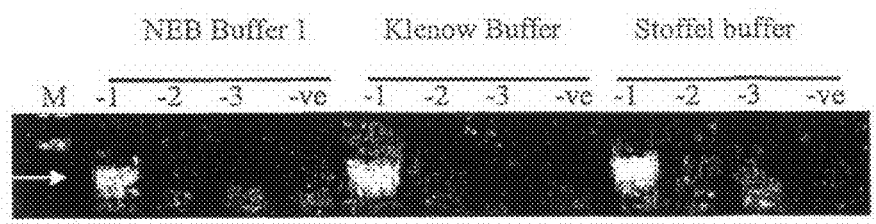
FIG. 9 shows results of isothermal amplification using oligonucleotide primers containing ribonucleotides in combination with RNase H and Klenow exo-.

Ten µl of the amplified product were mixed with 10 µl of water and the amplification products resolved on a E-Gel 48 4% agarose (HR) gel (Invitrogen Cat# G8080-04) and the gel run using the Powerbase™. Markers (M) were the E-gel low range quantitative DNA ladder (Invitrogen cat#12373-031. Gels were visualised under UV irradiation using the Kodak UVIdoc EDAS 290 system and results shown in FIG. 9.

Amplification Using 8-Deoxyguanine

Isothermal amplifications were carried out using a primer set directed to the detection of the following target DNA sequences;

(SEQ ID NO 1)
5' AGGGAATTTTTTTTCGCGATGTTTCGGCGCGTTAGTTCGTTGCGTAT
ATTTCGTTGCGGTTTTTTTTTGGTTTTTTCGGTTAGTTGCGCGGCGATT
TCGGGGATTTTAG 3'

P#1
(SEQ ID NO 26)
5' AGGGAATTTTTTTTCGCNNNGATGTTTCGGCGCGTTAGTTCGT

P#2
(SEQ ID NO 27)
5' CTAAAATCCCCGAAATCGGCCNNNGCGCAACTAACCGAAAAAAC non-Regular Base was NNNG=8-deoxyguanine.

Primers were synthesised using standard phosphoamidite chemistry.

Amplification was carried out under the following conditions:

50 ng of each of the above oligonucleotide primers, 500 µM dNTPs, 1 mM MgCl$_2$, 1U Fpg, 2.5U Klenow Exo- in 9 µl of X10 reaction buffer X1 Stoffel buffer (Perkin Elmer-Applied Biosystems, Foster City, USA).

Ten-fold serial dilutions of target DNA were prepared ranging from $10^{-1}$ to $10^{-3}$. One µl of the diluted DNA was then added to the above reaction mixture and incubated for 4 hours at 42° C.

Figure 10:
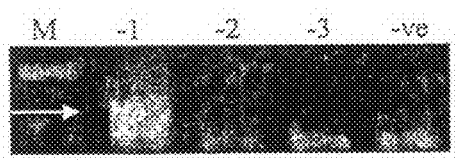
FIG. 10 shows results of isothermal amplification using oligonucleotide primers containing 8-deoxyguanine in combination with fpg and Klenow exo-.

Ten µl of the amplified product were mixed with 10 µl of water and the amplification products resolved on a E-Gel 48 4% agarose (HR) gel (Invitrogen Cat# G8080-04) and the gel run using the Powerbase™. Markers (M) were the E-gel low range quantitative DNA ladder (Invitrogen cat#12373-031. Gels were visualised under UV irradiation using the Kodak UVIdoc EDAS 290 system and results are shown in FIG. 10.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for isothermal DNA amplification, the method comprising:
    providing to the DNA to be amplified an amplification mix comprising:
        a first primer being at least partially complementary to a region of DNA having a CpG dinucleotide, the first primer containing at least one deoxyinosine and does not include a ribonucleotide,
        a second primer being at least partially complementary to a region of DNA having a CpG dinucleotide, the first primer containing at least one deoxyinosine and does not include a ribonucleotide,
        an exonuclease deficient DNA polymerase,
        an enzyme capable of strand displacement,
        an enzyme that recognises a deoxyinosine in double-stranded DNA and causes a nick in one DNA strand at or near the deoxyinosine; and
        amplifying the DNA substantially without thermal cycling, wherein inosine substitutes the position of guanine in a CpG dinucleotide of the DNA.

2. The method according to claim 1 wherein the DNA is denatured prior to, during, or after addition of the amplification mix.

3. The method according to claim 1 wherein the first primer is at least partially complementary to a region of a first strand of DNA and the second primer is at least partially complementary to a region of DNA of a second strand of DNA.

4. The method according to claim 1 wherein the first and second primers are selected from the group consisting of oligonucleotides, oligonucleotide analogues, PNA/oligonucleotides, and INA/oligonucleotides.

5. The method according to claim 4 wherein the primers are deoxyoligonucleotides.

6. The method according to claim 1 wherein the primers contain two or more deoxyinosines.

7. The method according to claim 1 wherein when the primer binds to DNA it forms a site recognised by the nicking enzyme.

8. The method according to claim 1 wherein the strand displacement enzyme is selected from the group consisting of Helicases, AP endonucleases, and mismatch repair enzymes of any enzyme capable of stand displacement.

9. The method according to claim 1 wherein the DNA polymerase also has strand displacement capability.

10. The method according to claim 1 wherein the nicking enzyme is Endonuclease V.

11. The method according to claim 1 further including additives required for DNA amplification.

12. The method according to claim 11 wherein the additives are selected from the group consisting of nucleotides, buffers or diluents containing magnesium or manganese ions, co-factors, single stranded binding proteins, and T4gp32.

13. The method according to claim 1 wherein amplification is carried out at a temperature of from 20° C. to 75° C.

14. The method according to claim 13 wherein the temperature is about 42° C.

15. The method according to claim 1 wherein the DNA is pre-treated with a modifying agent which modifies cytosine bases but does not modify 5'-methyl-cytosine bases under conditions to form single stranded modified DNA.

16. The method according to claim 15 wherein the modifying agent is selected from bisulphite, acetate or citrate and treatment does not result in substantial DNA fragmentation.

17. The method according to claim 16 wherein the modifying agent is sodium bisulphite.

18. A method for amplifying DNA, the method comprising:
    a. hybridizing a primer to one strand of said DNA to form a primer-template complex, wherein said primer contains an inosine base and being at least partially complementary to a region of said DNA having a CpG dinucleotide;
    b. extending the 3' end of said primer in the presence of an exonuclease deficient DNA polymerase to generate a double stranded molecule having a first newly synthesized strand containing an inosine base, wherein inosine substitutes the position of guanine in a CpG dinucleotide of said DNA;
    c. causing a nick at or near the inosine base of the first newly synthesized strand using a nicking enzyme;
    d. displacing the first newly synthesized strand and regenerating the inosine base-containing primer with a DNA polymerase having strand displacement activity, and forming newly synthesized strands of DNA; and
    e. repeating steps (c) and (d) to thereby amplify the DNA via successive rounds of amplification.

19. The method of claim 18, wherein said template DNA is genomic DNA.

20. The method of claim 18, wherein said primer is a gene specific primer.

21. The method of claim 18, wherein said primer is a locus specific primer.

22. The method of claim 18, wherein said nick does not remove said inosine base.

23. The method of claim 18, wherein said nick occurs about 2-3 nucleotides downstream of said 3' end of said inosine base.

24. The method of claim 18, wherein said DNA polymerase with strand displacement function is selected from the group consisting of Klenow fragment, Bst polymerase, and phi29 polymerase.

25. The method of claim 18, wherein said DNA polymerase is active at a temperature between 30° C. and 80° C.

26. The method according to claim 24, wherein said Bst DNA polymerase is active between 50° C. to 65° C.

27. The method according to claim 24, wherein said phi29 DNA polymerase is active at between 30° C. and 1° C.

28. The method according to claim 18, wherein said nicking enzyme is an Endonuclease V.

29. The method of claim 28, wherein said Endonuclease V is from *Escherichia coli*.

30. The method of claim 29, wherein said Endonuclease V is a thermal stable version.

31. The method according to claim 30, wherein said Endonuclease V is active between 30° C. and 60° C.

32. The method according to claim 30, wherein said Endonuclease V is active at a temperature between 30° C. and 1° C.

33. The method of claim 18, wherein prior to step (a) the DNA template strand is denatured.

34. The method according to claim 18, wherein steps (c) and (d) are performed in same buffer.

35. The method of claim 18, wherein steps (a)-(d) are performed simultaneously in a single reaction.

36. The method of claim 18, wherein step (c) comprises generating a nick in the extended primer using an endonuclease that generates nicks 3' of said inosine base.

37. The method of claim 18, wherein steps (a)-(d) are performed under isothermal conditions.

38. A method for amplifying a template DNA, the method comprising:
    a. binding a primer containing an inosine base to the template DNA at regions having CpG dinucleotides;

b. extending said primer in the presence of an exonuclease deficient DNA polymerase with strand displacement capability to generate a double stranded molecule having a first newly synthesized strand containing a plurality of inosine bases, wherein the inosine bases substitute the positions of guanine in the CpG dinucleotides of the template DNA;

c. causing nicks at or near the inosine bases of the first newly synthesized strand using a nicking enzyme;

d. extending from the nicks with a DNA polymerase having strand displacement activity to generate multiple copies of the target; and e. repeating steps (c) and (d) to thereby amplify the DNA via successive rounds of amplification.

39. A method of amplifying a nucleic acid, the method comprising:

binding a first primer containing an inosine base to one strand of DNA at a region having a CpG dinucleotide;

extending said primer with an exonuclease deficient DNA polymerase to form a double stranded molecule having a first newly synthesized strand comprising an inosine base, wherein the inosine base substitutes the position of guanine in the CpG dinucleotide of the DNA;

nicking said first newly synthesized strand near the position of said inosine base;

displacing the first newly synthesized strand with a DNA polymerase; and continuing the process to repeatedly form newly synthesized strands of DNA.

40. A method for obtaining multiple copies of a template DNA strand, the method comprising:

a. annealing a primer to said template DNA strand at a region of the template DNA having a CpG dinucleotide to form a primer-template complex, wherein said primer comprises an inosine base and the inosine base substitutes the position of guanine in the CpG dinucleotide of the DNA;

b. extending the 3' end of said primer in the presence of an exonuclease deficient DNA polymerase activity to generate a first extended primer that comprises a primer portion and a first copy of the template sequence;

c. generating a nick in the extended primer using an endonuclease that generates nicks 3' of said inosine base;

d. extending the portion of the primer region that is 5' of the nick from the nick in the presence of the DNA polymerase, thereby displacing the portion of the extended primer that is 3' of the nick, including the first copy of the template DNA sequence and generating a second extended primer comprising a primer region and a second copy of the template DNA sequence; wherein said second extended primer comprises an inosine base; and e. repeating steps (c) and (d) at least once to obtain multiple copies of the template DNA strand.

41. The method of claim 40, wherein said template DNA is genomic DNA.

42. The method of claim 40, wherein said primer is a locus specific primer.

43. The method of claim 40, wherein said nick does not remove said inosine base.

44. The method of claim 40, wherein said nick occurs about 2-3 nucleotides downstream of said 3' end of said inosine base.

45. The method of claim 40, wherein said DNA polymerase with strand displacement function is selected from the group consisting of Klenow fragment, Bst polymerase, and phi29 polymerase.

46. The method of claim 40, wherein said DNA polymerase is active at a temperature between 30° C. and 80° C.

47. The method according to claim 45, wherein said Bst DNA polymerase is active between 50° C. to 65° C.

48. The method according to claim 45, wherein said Phi29 DNA polymerase is active at between 30° C. and 1° C.

49. The method according to claim 40, wherein said endonuclease is an Endonuclease V.

50. The method of claim 49, wherein said Endonuclease V is from *Escherichia coli*.

51. The method of claim 50, wherein said Endonuclease V is a thermal stable version.

52. The method according to claim 51, wherein said Endonuclease V is active between 30° C. and 60° C.

53. The method according to claim 49, wherein said Endonuclease V is active at a temperature between 30° C. and 1° C.

54. The method of claim 40, wherein prior to step (a) the DNA template strand is denatured.

55. The method according to claim 40, wherein steps (c) and (d) are performed in same buffer.

56. The method of claim 40, wherein steps (a)-(d) are performed simultaneously in a single reaction.

57. The method of claim 40, wherein steps (a)-(d) are performed under isothermal conditions.

58. A method for amplifying a template DNA, the method comprising:

a. annealing a primer containing an inosine base to the template DNA at a region of the template DNA having a CpG dinucleotide;

b. extending the primer in the presence of a strand displacing DNA polymerase and deoxyinosine triphosphate to generate a first extension product comprising inosine, wherein the inosine base substitutes the position of guanine in the CpG dinucleotide of the template DNA;

c. incubating the product of step (b) with an endonuclease V to generate nicks in the first primer extension product at positions 3' of the incorporated inosine;

d. extending from the nicks with a strand displacing enzyme to generate second extension products; and e. repeating steps (c) and (d) at least once to generate amplified template DNA.

* * * * *

UNITED STATES PATENT AND TRADEMARK OFFICE
CERTIFICATE OF CORRECTION

PATENT NO.         : 8,431,347 B2
APPLICATION NO.    : 11/919443
DATED              : April 30, 2013
INVENTOR(S)        : Millar et al.

It is certified that error appears in the above-identified patent and that said Letters Patent is hereby corrected as shown below:

On the Title Page

In column 2 (page 2, item 56) at line 68 (approx.), Under Other Publications, change "Bioconjugate Chern." to --Bioconjugate Chem.--.

In column 1 (page 3, item 56) at line 13, Under Other Publications, change "Transdifferentation." to --Transdifferentiation.--.

In column 1 (page 3, item 56) at line 23, Under Other Publications, change "deoxyoxadenosine" to --deoxyadenosine--.

In column 1 (page 3, item 56) at line 44, Under Other Publications, change "Bioconjugate Chern.," to --Bioconjugate Chem.,--.

In column 1 (page 3, item 56) at lines 56-57, Under Other Publications, change "Bioconjugate Chern.," to --Bioconjugate Chem.,--.

In column 1 (page 3, item 56) at line 71, Under Other Publications, change "Epigentic" to --Epigenetic--.

In column 2 (page 3, item 56) at line 2, Under Other Publications, change "methylation-sensitive QPCR." to --methylation-sensitive PCR.--.

In column 2 (page 3, item 56) at line 25, Under Other Publications, change "DNA sequencs" to --DNA sequence--.

In column 2 (page 3, item 56) at line 54, Under Other Publications, change "Agricultureal" to --Agricultural--.

In column 1 (page 4, item 56) at line 21, Under Other Publications, change "Scuebces," to --Sciences,--.

In column 1 (page 4, item 56) at line 34, Under Other Publications, change "sensititive" to --sensitive--.

Signed and Sealed this
Twenty-fourth Day of June, 2014

Michelle K. Lee
*Deputy Director of the United States Patent and Trademark Office*

CERTIFICATE OF CORRECTION (continued)
U.S. Pat. No. 8,431,347 B2

In the Specification

In column 2 at lines 63-64, Change "phosphorthioate" to --phosphorothioate--.

In column 2 at lines 64-65, Change "hemi-phosphorthioate" to --hemi-phosphorothioate--.

In column 3 at line 6, Change "N.BstNB1" to --N.BstNBI--.

In column 3 at line 10, Change "Mly1" to --MlyI--.

In column 3 at line 23, Change "Spears P., A.," to --Spears P. A.,--.

In column 4 at line 9 (approx.), Change "phosphorodithiates," to --phosphorodithioates,--.

In column 4 at line 19 (approx.), Change "(Unest NS," to --(Unest A/S,--.

In column 4 at line 43 (approx.), Change "polymersae" to --polymerase--.

In column 4 at line 45, Change "9° N," to --9° Nm--.

In column 4 at line 59, Change "MO212S)," to --M0212S),--.

In column 4 at line 60, Change "large., fragment" to --large fragment--.

In column 4 at line 61, Change "MO275S)," to --M0275S),--.

In column 4 at line 61, Change "MO257S)," to --M0257S),--.

In column 4 at line 62, Change "MO259S)," to --M0259S),--.

In column 4 at line 63, Change "MO253S)," to --M0253S),--.

In column 4 at line 64, Change "MO260S)" to --M0260S)--.

In column 4 at line 65, Change "MO269S)" to --M0269S)--.

In column 5 at line 11, Change "MO268S)," to --M0268S),--.

In column 5 at line 13, Change "MO299S)," to --M0299S),--.

In column 5 at line 45 (approx.), Change "Sodium bisulphite.(NaHSO$_3$)" to --Sodium bisulphite (NaHSO$_3$)"--.

In column 7 at line 12 (approx.), Change "these Matters" to --these matters--.

In column 7 at line 43, Change "primers" to --primers.--.

In column 7 at line 61, Change "8 deokyguanine" to --8 deoxyguanine--.

In column 8 at line 5, Change "phosphoamidite" to --phosphoramidite--.

In column 8 at line 10 (approx.), Change "Endonuclease V" to --Endonuclease V.--.

In column 8 at line 16 (approx.), Change "hOGG1" to --hOGG1.--.

In column 8 at line 19, Change "RNase H" to --RNase H.--.

In column 8 at line 59, Change "DNA (C);" to --DNA (C),--.

In column 9 at line 23 (approx.), Change "parried" to --carried--.

In column 9 at line 52, Change "phosphoamidite" to --phosphoramidite--.

In column 10 at line 9, Change "110 by" to --110 bp--.

In column 10 at line 51, Change "phosphoamidite" to --phosphoramidite--.

CERTIFICATE OF CORRECTION (continued)
U.S. Pat. No. 8,431,347 B2

In column 10 at line 59, Change "110 by" to --110 bp--.

In column 11 at line 43 (approx.), Change "25, cycles" to --25 cycles--.

In column 11 at line 45 (approx.), Change "110 by" to --110 bp--.

In column 11 at lines 59-60, Change "Powerbase™:" to --Powerbase™.--.

In column 13 at line 10, Change "phosphoamidite" to --phosphoramidite--.

In column 13 at line 28, Change "Powerbase™," to --Powerbase™.--.

In column 13 at line 48 (approx.), Change "phosphoamidite" to --phosphoramidite--.

In column 14 at line 43, Change "phosphoamidite" to --phosphoramidite--.

In column 14 at line 47, Change "oligOnucleotide" to --oligonucleotide--.

In column 15 at line 18, Change "phosphoamidite" to --phosphoramidite--.

In column 16 at line 14, Change "phosphoamidite" to --phosphoramidite--.

In the Claims

In column 28 at line 42, In Claim 27, change "1° C." to --37° C.--.

In column 28 at line 52, In Claim 32, change "1° C." to --37° C.--.

In column 30 at line 17, In Claim 48, change "Phi29" to --phi29--.

In column 30 at line 18, In Claim 48, change "1° C." to --37° C.--.

In column 30 at line 28, In Claim 53, change "1° C." to --37° C.--.